(12) United States Patent
Babcock et al.

(10) Patent No.: US 8,617,604 B2
(45) Date of Patent: Dec. 31, 2013

(54) PHARMACEUTICAL COMPOSITIONS WITH ENHANCED PERFORMANCE

(75) Inventors: Walter Christian Babcock, Bend, OR (US); Dwayne Thomas Friesen, Bend, OR (US); David Kenneth Lyon, Bend, OR (US); Warren Kenyon Miller, Bend, OR (US); Daniel Tod Smithey, Bend, OR (US)

(73) Assignee: Bend Research, Inc., Bend, OR (US)

( * ) Notice: Subject to any disclaimer, the term of this patent is extended or adjusted under 35 U.S.C. 154(b) by 1407 days.

(21) Appl. No.: 11/795,747

(22) PCT Filed: Jan. 23, 2006

(86) PCT No.: PCT/IB2006/000293
§ 371 (c)(1),
(2), (4) Date: Nov. 19, 2007

(87) PCT Pub. No.: WO2006/082518
PCT Pub. Date: Aug. 10, 2006

(65) Prior Publication Data
US 2008/0064763 A1 Mar. 13, 2008

Related U.S. Application Data

(60) Provisional application No. 60/649,993, filed on Feb. 3, 2005, provisional application No. 60/649,994, filed on Feb. 3, 2005.

(51) Int. Cl.
*A61K 9/14* (2006.01)

(52) U.S. Cl.
USPC .............................. 424/484; 424/488

(58) Field of Classification Search
None
See application file for complete search history.

(56) References Cited

U.S. PATENT DOCUMENTS

| | | | |
|---|---|---|---|
| 4,652,442 A | 3/1987 | Hopfgartner et al. | |
| 4,795,641 A | 1/1989 | Kashdan | |
| 4,888,420 A | 12/1989 | Steiner et al. | |
| 6,548,555 B1 * | 4/2003 | Curatolo et al. | 514/772.4 |
| 7,741,374 B1 * | 6/2010 | Arnold et al. | 514/687 |
| 2002/0006443 A1 * | 1/2002 | Curatolo et al. | 424/486 |
| 2003/0054037 A1 * | 3/2003 | Babcock et al. | 424/486 |
| 2003/0054038 A1 | 3/2003 | Crew et al. | |
| 2003/0185891 A1 | 10/2003 | Crew et al. | |
| 2004/0185102 A1 | 9/2004 | Friesen et al. | |

FOREIGN PATENT DOCUMENTS

| | | |
|---|---|---|
| EP | A-0 219 426 | 4/1987 |
| EP | 1027886 A2 * | 8/2000 |
| EP | A-1 437 216 | 7/2004 |
| WO | WO/2005/115330 A | 12/2005 |

* cited by examiner

*Primary Examiner* — Susan Tran
(74) *Attorney, Agent, or Firm* — Chernoff Vilhauer McClung & Stenzel LLP

(57) ABSTRACT

Pharmaceutical compositions of a low-solubility drug and lower alkanoate-, phthalate- and trimellitate esters of hydroxypropyl methyl cellulose and lower alkanoate- and succinate esters of cellulose and methyl cellulose are disclosed that provide enhanced concentrations of the drug in a use environment.

8 Claims, 2 Drawing Sheets

PHARMACEUTICAL COMPOSITIONS WITH ENHANCED PERFORMANCE

CROSS-REFERENCE TO RELATED APPLICATIONS

This is a 371 of PCT/IB2006/000293 filed 23 Jan. 2006 and claims priority of U.S. Ser. Nos. 60/649,993 and 60/649,994, both filed 3 Feb. 2005.

BACKGROUND OF THE INVENTION

It has been suggested that hydroxypropyl methyl cellulose acetate phthalate (HPMCAP) and hydroxypropyl methyl cellulose acetate trimellitate (HPMCAT) may be used to form solid amorphous dispersions with low-solubility drugs, and that such dispersions should result in concentration enhancement (or improved bioavailability) of the drug in the dispersion in an aqueous environment of use. However, there has been no disclosure of the optimal degree of substitution of acetyl or phthalyl or trimellityl groups for either the HPMCAP or HPMCAT polymers.

The use of HPMCAP in physical admixtures with basic drugs has also been suggested for improving the bioavailability of such drugs. However, there has been no disclosure of the degree of substitution of acetyl or phthalyl groups for the HPMCAP polymer used in such admixtures.

Cellulose acetate succinate (CAS) was originally developed as an enteric polymer for coating pharmaceutical dosage forms. See U.S. Pat. No. 2,196,768. Enteric polymers are those that remain intact in the acidic environment of the stomach, preventing drug release therein, but degrade in the alkaline environment of the intestine so as to release drug in the intestine. Such polymers have also been used for matrix-type controlled-release dosage forms. See U.S. Pat. Nos. 4,652,442 and 4,795,641. However, there is no disclosure of the use of CAS for making a physical mixture or a solid dispersion of a low-solubility drug in either of these patents, nor is there any recognition of the impact of the degree of substitution (DOS) of the cellulose on the bioavailability of the drugs in such compositions.

U.S. Pat. No. 4,888,420 discloses the use of cellulose acetate and water-soluble derivatives thereof such as cellulose acetate phthalate and CAS to prepare highly porous microspheres that may be used as a carrier for controlled release of fragrances and drugs such as aspirin and prednisone. The '420 patent does not disclose the formation of physical mixtures or solid dispersions of CAS and a low-solubility drug, and although it does disclose a DOS of 0.5-1.0 for cellulose acetate, there is no disclosure of any particular DOS for any substituent group other than acetate, and there is no recognition of the impact of DOS on the bioavailability of drugs incorporated into the microspheres.

No reference has been found in the literature to methyl-substituted CAS (MCAS) in pharmaceutical applications.

Thus, while pharmaceutical formulations of drugs and HPMCAP, HPMCAT, and CAS polymers have been suggested, there has been no recognition of either the impact or importance of the degrees of substitution of acetyl, phthalyl, trimellityl, succinyl, and methyl groups relative to enhancing the concentration of the drug in a use environment or improving the drug's bioavailability. What is desired therefore are HPMCAP, HPMCAT, CAS, and MCAS polymers specifically designed for improving the dissolved drug concentration in a pharmaceutical composition.

BRIEF SUMMARY OF THE INVENTION

The present invention provides polymers of hydroxypropyl methyl cellulose alkanyl phthalate (HPMCA$_{lk}$P), hydroxypropyl methyl cellulose alkanyl trimellitate (HPMCA$_{lk}$T), cellulose alkanyl succinate (CA$_{lk}$S), and methyl cellulose alkanyl succinate (MCA$_{lk}$S) with a combination of substituent levels that have utility when used in pharmaceutical compositions. As used herein, the term "alkanyl" or its abbreviation "A$_{lk}$" means a carbonyl-containing moiety selected from acetyl, propionyl, butyryl and isomers thereof.

Thus, in one aspect, the invention provides a composition comprising an HPMCA$_{lk}$P polymer wherein the degree of substitution of alkanyl groups (DOS$_{Alk}$) and the degree of substitution of phthalyl groups (DOS$_P$) on the HPMCA$_{lk}$P are
DOS$_{Alk}$≥about 0.3, preferably ≥about 0.4 and
DOS$_P$≥about 0.05, preferably ≥about 0.10.

In another aspect, the invention comprises such an HPMCA$_{lk}$P polymer and a low-solubility drug, the drug having a minimum aqueous solubility of about 0.5 mg/mL or less, wherein the polymer and the drug are intimately mixed.

In another aspect, the invention provides a composition comprising an HPMCA$_{lk}$T polymer wherein DOS$_{Alk}$ and DOS$_T$ on the HPMCA$_{lk}$T are
DOS$_{Alk}$≥about 0.5, preferably ≥about 0.6, and
DOS$_T$≥about 0.03, preferably ≥about 0.05.

In another aspect, the invention comprises such an HPMCA$_{lk}$T polymer and a low-solubility drug, the drug having a minimum aqueous solubility of about 0.5 mg/mL or less, wherein the polymer and the drug are intimately mixed.

In yet another aspect, the invention provides pharmaceutical compositions of a low-solubility drug having a minimum aqueous solubility of about 0.5 mg/mL or less and CA$_{lk}$S polymers wherein DOS$_{Alk}$ and the degree of substitution of succinyl groups (DOS$_S$) on the CA$_{lk}$S are
DOS$_{Alk}$≥about 1.0, preferably ≥about 1.25, and
DOS$_S$≥about 0.2, preferably ≥about 0.25.

In still another aspect, the invention provides a composition comprising an MCA$_{lk}$S polymer wherein the combined degree of substitution of methoxy groups and alkanyl groups (DOS$_{M-Alk}$) and DOS$_S$ on the MCA$_{lk}$S are
DOS$_{M+Alk}$≥about 1.0, preferably ≥about 1.25, and
DOS$_S$≥about 0.2, preferably, ≥about 0.25.

In another aspect, the invention comprises such an MCA$_{lk}$S polymer and a low-solubility drug, the drug having a minimum aqueous solubility of about 0.5 mg/mL or less, wherein the polymer and the drug are intimately mixed.

The invention provides one or more of the following advantages. The HPMCA$_{lk}$P, HPMCA$_{lk}$T, CA$_{lk}$S, and MCA$_{lk}$S polymers have a novel combination of substituent degrees of substitution specifically tailored to provide utility for pharmaceutical compositions. When used to form solid amorphous dispersions of low-solubility drugs, and in particular, of hydrophobic drugs, such polymers provide enhanced physical stability of the drug therein and enhanced concentrations of dissolved drug in a use environment. When used in combination with drugs that are prone to rapid crystallization from supersaturated aqueous solutions, such polymers are particularly effective at sustaining high drug concentrations and thereby enhancing absorption of drug in vivo. Such polymers are also useful in forming blends and mixtures with solubility-improved forms of low-solubility drugs, resulting in concentration enhancements of the same.

The foregoing and other objectives, features, and advantages of the invention will be more readily understood upon consideration of the following detailed description of the invention.

Figure 1:
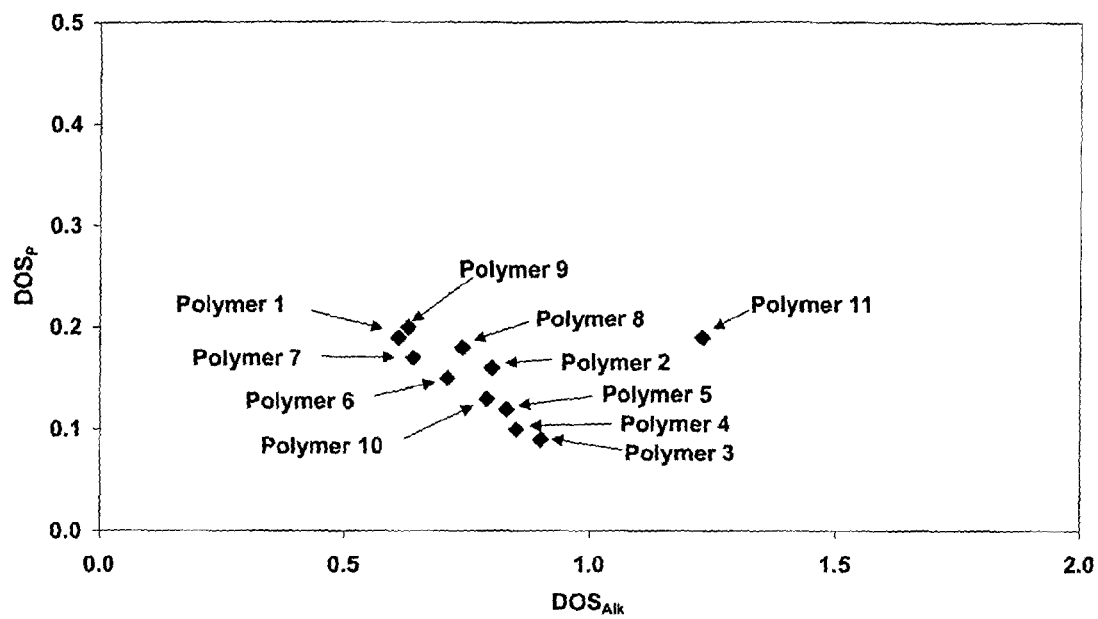
FIG. 1 is a plot of the DOS$_P$ versus the DOS$_{Alk}$ (for several HPMCA$_{lk}$P polymers synthesized in the Examples.
Figure 2:
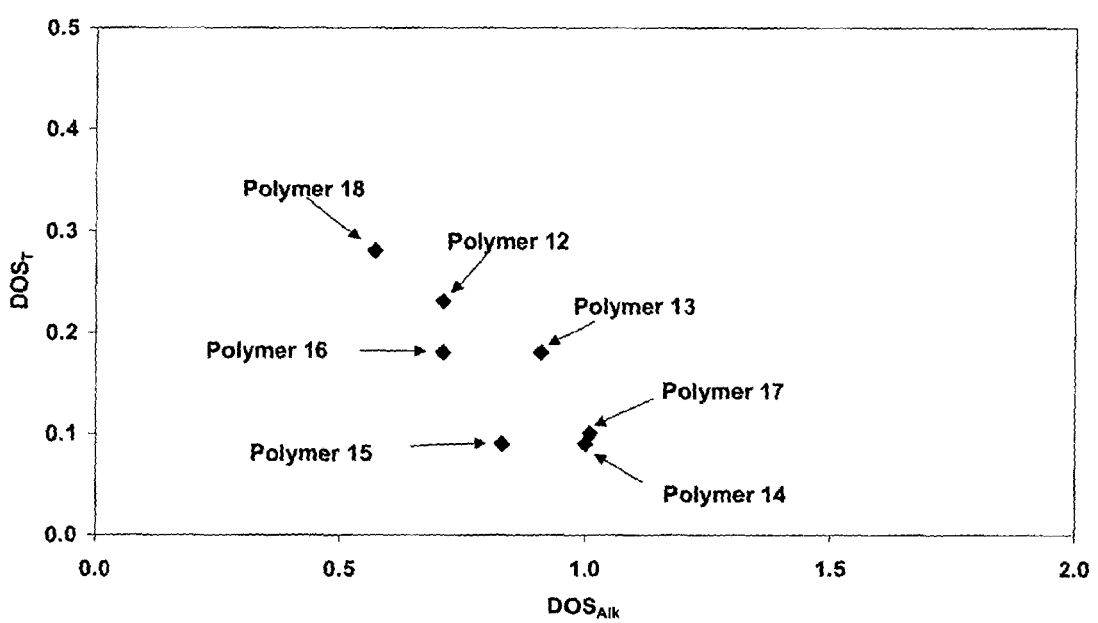
FIG. 2 is a plot of the DOS$_T$ versus the DOS$_{Alk}$ for several HPMCA$_{lk}$T polymers synthesized in the Examples.
Figure 3:
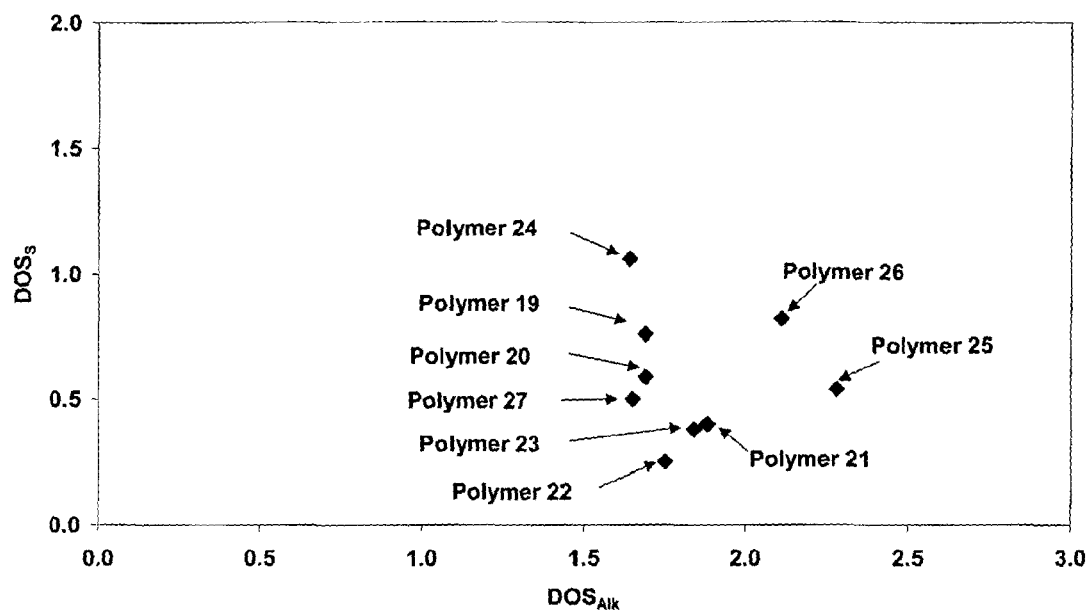
FIG. 3 is a plot of the $DOS_S$ versus the $DOS_{Alk}$ for several $CA_{lk}S$ polymers synthesized in the Examples.
Figure 4:
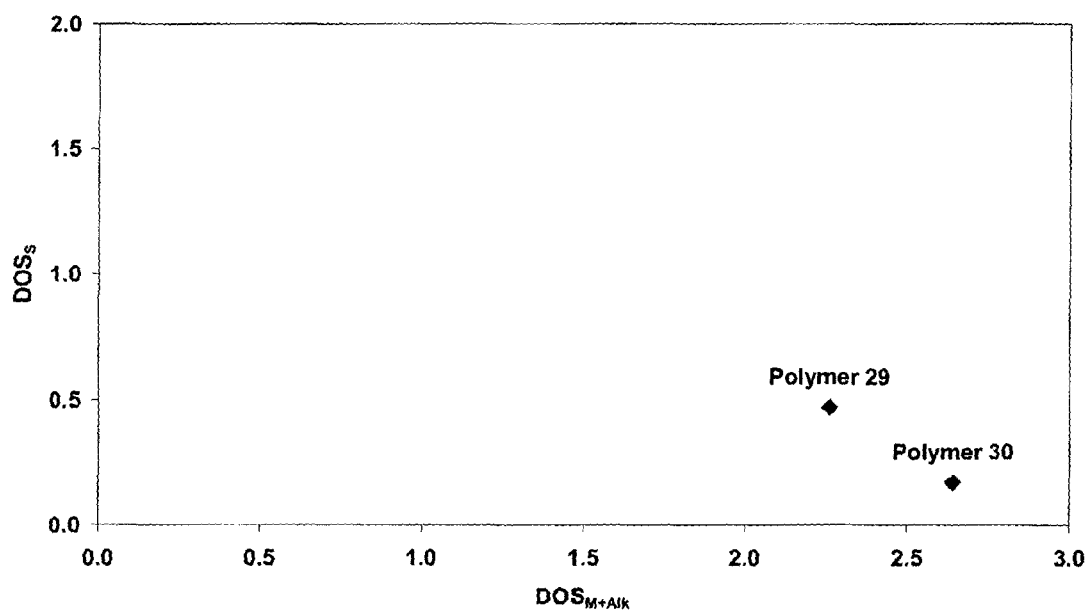
FIG. 4 is a plot of the $DOS_S$ versus the $DOS_{M+Alk}$ for several $MCA_{lk}S$ polymers synthesized in the Examples.

DETAILED DESCRIPTION OF PREFERRED EMBODIMENTS $HPMCA_{lk}P$, $HPMCA_{lk}T$, $CA_{lk}S$, and $MCA_{lk}S$ are substituted cellulosic polymers. By "substituted cellulosic polymer" is meant a cellulose polymer that has been modified by reaction of at least a portion of the hydroxyl groups on the saccharide repeat units with a compound to form an ester-linked or an ether-linked substituent. Cellulose has the following general repeat unit.

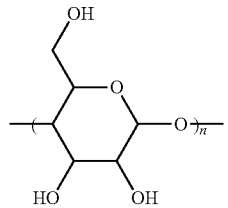

$HPMCA_{lk}P$ and $HPMCA_{lk}T$ both contain 2-hydroxypropoxy groups (—$OCH_2CH(CH_3)OH$, hereinafter referred to as hydroxypropoxy groups) ether-linked to the saccharide repeat unit by substitution on any hydroxyl group present on the repeat unit, or linked to a hydroxyl group on another hydroxypropoxy group, as shown below.

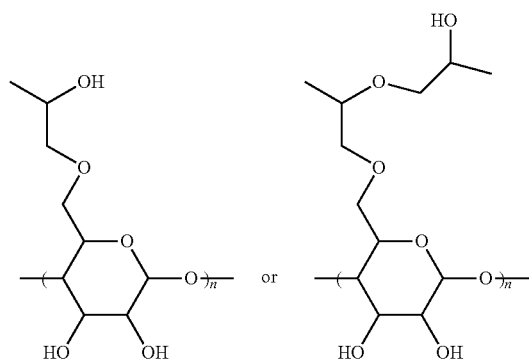

$HPMCA_{lk}P$, $HPMCA_{lk}T$, and $MCA_{lk}S$ also contain methoxy groups (—$OCH_3$), ether-linked to the saccharide repeat unit by substitution on any hydroxyl group present on the repeat unit, as shown below.

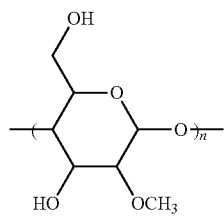

The $HPMCA_{lk}P$, $HPMCA_{lk}T$, $CA_{lk}S$, and $MCA_{lk}S$ polymers of the invention may also contain alkanyl groups (—COR) ester-linked to the saccharide repeat unit by substitution on any hydroxyl group present on the repeat unit, as shown below, where R is methyl, ethyl or propyl.

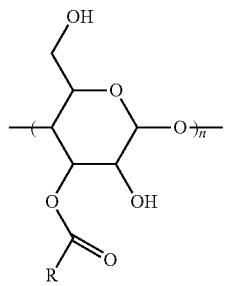

$HPMCA_{lk}P$ also contains phthalyl groups (—$COC_6H_4COOH$) ester-linked to the saccharide repeat unit by substitution on any hydroxyl group present on the repeat unit, as shown below.

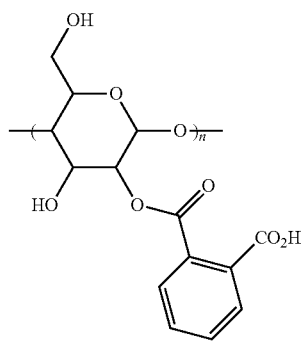

$HPMCA_{lk}T$ also contains trimellityl groups (—$COC_6H_3(COOH)_2$) ester-linked to the saccharide repeat unit by substitution on any hydroxyl group present on the repeat unit, as shown below.

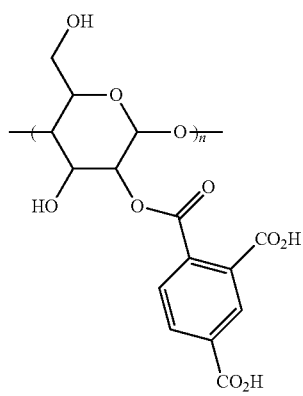

or

-continued

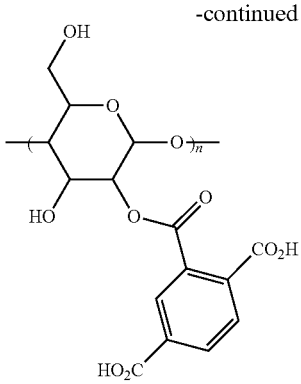

CA$_{Ik}$S and MCA$_{Ik}$S also contain succinyl groups (—COC$_4$H$_4$COOH) ester-linked to the saccharide repeat unit by substitution on any hydroxyl group present on the repeat unit, as shown below.

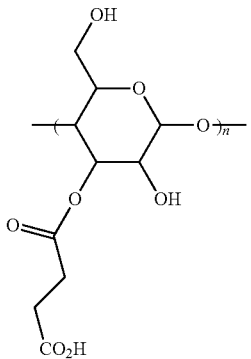

Thus, as used in the specification and claims, by "HPMCA$_{Ik}$P" and "HPMCA$_{Ik}$T" are meant cellulosic polymers substituted with hydroxypropoxy groups, methoxy groups, alkanyl groups, phthalyl groups (in the case of HPMCA$_{Ik}$P), and trimellityl groups (in the case of HPMCA$_{Ik}$T). Other substituents can be included on the polymers in small amounts, provided they do not materially affect the polymers' performance and properties.

Additionally, as used in the specification and claims, by "CA$_{Ik}$S" and "MCA$_{Ik}$S" are meant cellulosic polymers substituted with alkanyl groups and succinyl groups (in the case of CA$_{Ik}$S), and alkanyl, succinyl and methoxy groups (in the case of MCA$_{Ik}$S), respectively. Other substituents can be included on the polymers in small amounts, provided they do not materially affect the polymers' performance and properties.

HPMCA$_{Ik}$P and HPMCA$_{Ik}$T

The amount of any one substituent on the HPMCA$_{Ik}$P and HPMCA$_{Ik}$T (collectively referred to hereinafter as 'HPMCA$_{Ik}$P/CA$_{Ik}$T' when discussing common characteristics) is characterized by its degree of substitution (DOS) on the polymer, meaning the average number of a given substituent that is substituted on the saccharide repeat unit of the cellulose chain. The substituent may be attached directly to the saccharide repeat unit by substitution for any of the three hydroxyls on the saccharide repeat unit, or it may be attached through a hydroxypropoxy substituent, the hydroxypropoxy substituent being attached to the saccharide repeat unit by substitution for any of the three hydroxyls on the saccharide repeat unit. For example, an alkanyl substituent may be attached to a hydroxyl group on the saccharide repeat unit or to the hydroxyl group on a hydroxypropoxy substituent, as shown below where R is methyl, ethyl or propyl.

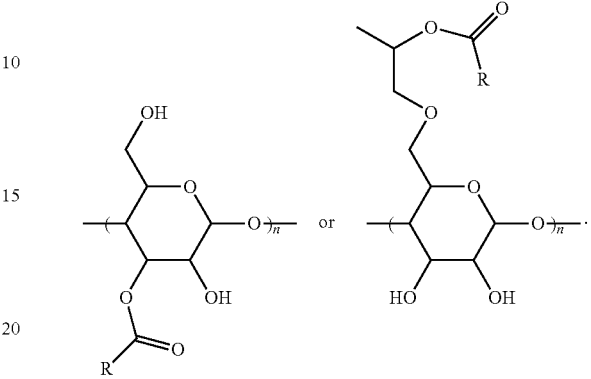

DOS represents the average number of a given substituent on the saccharide repeat unit. Thus, if on average 1.3 hydroxyls on the saccharide repeat unit are substituted with a methoxy group, DOS$_M$ would be 1.3. As another example, if on average two of the three hydroxyls on the saccharide repeat unit are substituted with a methoxy group, the DOS$_M$ would be 2.0. In another example, if one of the three hydroxyls on the saccharide repeat unit is substituted with an hydroxypropoxy group, and one of the remaining two hydroxyls on the saccharide repeat unit is substituted with a methoxy group and the hydroxyl on the hydroxypropoxy group is substituted with a methoxy group, the degree of substitution of hydroxypropoxy groups (DOS$_{HP}$) would be 1.0 and the DOS, would be 2.0.

Suitable methods to vary the DOS of various substituents on HPMCA$_{Ik}$P/CA$_{Ik}$T, suitable drugs, and exemplary methods for forming pharmaceutical compositions are described in detail below.

The inventors have found that when low-solubility drugs, particularly those that are hydrophobic, are formed into compositions with novel grades of HPMCA$_{Ik}$P/CA$_{Ik}$T polymers with particular ranges of substituent levels, the compositions provide concentration enhancement of the drugs when administered to an aqueous environment of use.

In particular, the inventors have found that HPMCA$_{Ik}$P polymers having the following DOS provide concentration enhancement of low-solubility drugs when used to formulate pharmaceutical compositions of such drugs:
DOS$_{Alk}$≥about 0.3, preferably ≥about 0.4; and
DOS$_P$≥about 0.05, preferably ≥about 0.1.

The inventors have further found that HPMCA$_{Ik}$T polymers having the following DOS provide concentration enhancement of low-solubility drugs when used to formulate pharmaceutical compositions of such drugs:
DOS$_{Alk}$≥about 0.5, preferably ≥about 0.6; and
DOS$_T$≥about 0.03, preferably ≥about 0.05.

The HPMCA$_{Ik}$P/CA$_{Ik}$T polymers also preferably have a DOS$_M$ ranging from about 1.0 to about 2.15. Within this range, the DOS$_M$ may be at least about 1.7, preferably at least about 1.75. The DOS$_M$ may also be about 2.1 or less, or even 2.0 or less. The inventors have found that HPMCA$_{Ik}$P/CA$_{Ik}$T polymers with these degrees of substitution of methoxy groups have utility for pharmaceutical formulations.

The $DOS_{HP}$ preferably ranges from about 0.05 to about 0.4. Within this range, the $DOS_{HP}$ may also range from about 0.15 to about 0.30. The inventors have found that $HPMCA_{lk}P/CA_{lk}T$ polymers with these degrees of substitution of hydroxypropoxy groups have utility for pharmaceutical formulations.

In general, and without wishing to be bound by any particular theory, it is believed that a principal reason the $HPMCA_{lk}P/CA_{lk}T$ polymers of the invention provide concentration enhancement of low-solubility drugs is that they are amphiphilic, containing relatively large amounts of both hydrophobic and hydrophilic groups. More specifically, in comparison to hydroxypropyl methyl cellulose phthalate (HPMCP), a known polymer for making solid dispersions of low-solubility drugs, the addition of alkanyl substituents (acetyl, propionyl, and butyryl) results in more hydrophobic regions on the polymer, resulting in more surface area to associate with a low-solubility and/or hydrophobic drug, which in turn leads to improved concentration enhancement. Compared to commercially available hydroxypropyl methyl cellulose acetate succinate (HPMCAS), another known polymer for making solid dispersions of low-solubility drugs, the phthalate and trimellitate groups have lower pKa values than succinate groups. As a result, more alkanyl groups can be added to an $HPMCA_{lk}P/CA_{lk}T$ polymer while maintaining a high aqueous-solubility, at any given pH, than an HPMCAS polymer having the same DOS of succinate as the phthalate or trimellitate DOS. $HPMCA_{lk}T$ has an additional advantage in that for each trimellitate substituent, two ionizable groups are obtained (in comparison to succinate and phthalate groups, which only provide one ionizable group each). Thus, $HPMCA_{lk}T$ polymers have a higher solubility for the same degree of substitution, and so can be made to be more amphiphilic, resulting in improved concentration enhancement.

The inventors have discovered that pharmaceutical compositions of drugs made with polymers that meet these criteria provide concentration enhancement or improved physical stability or both relative to control compositions as outlined herein.

The inventors have also discovered that solid amorphous dispersions of hydrophobic drugs and $HPMCA_{lk}P/CA_{lk}T$ with improved physical stability can be obtained by reducing the difference in solubility parameter between the drug and the polymer. Without wishing to be bound by any particular theory or mechanism of action, it is believed that when the difference in solubility parameter between the $HPMCA_{lk}P/CA_{lk}T$ and the drug is low, the free energy of mixing of the polymer/drug dispersion is low. The lower the free energy of mixing for the dispersion, the higher the thermodynamic solubility of the drug in the polymer. This means that for a given drug loading in a dispersion, the lower the difference in solubility parameter between the drug and polymer, the more physically stable the dispersion will be, i.e., It will either be more thermodynamically stable or will have a lower rate of phase separation into a drug-rich phase and a drug-poor phase, as detailed below. Alternatively, a dispersion with a higher drug loading can be formed that has the same physical stability as a dispersion made at a lower drug loading, but with a larger difference in solubility parameter. Methods to calculate the solubility parameter of drugs and $HPMCA_{lk}P/CA_{lk}T$ based on the DOS are described herein.

$CA_{lk}S$ AND $MCA_{lk}S$

The amount of any one substituent on the $CA_{lk}S$ and $MCA_{lk}S$ polymers of the invention (collectively referred to hereinafter as "$CA_{lk}S/MCA_{lk}S$" when discussing common characteristics) are characterized by the DOS on the polymers, meaning the average number of a given substituent that is substituted on any of the three hydroxyls on the saccharide repeat unit. As an example, if on average two of the three hydroxyls on the saccharide repeat unit are substituted with a methoxy group, the degree of substitution of methoxy groups ($DOS_M$) would be 2.0. Likewise, if on average 1.3 hydroxyls on the saccharide repeat unit are substituted with a methoxy group, $DOS_M$ would be 1.3.

The inventors have found that when low-solubility drugs, particularly those that are hydrophobic, are formed into compositions with the particular grades of $CA_{lk}S/MCA_{lk}S$ polymers having the particular DOS ranges of the invention, the compositions provide concentration enhancement of the drugs when administered to an aqueous environment of use.

In particular, the inventors have found that $CA_{lk}S$ polymers having the following DOS provide concentration enhancement of low-solubility drugs when used to formulate pharmaceutical compositions of such drugs:

$DOS_{Alk} \geq$ about 1.0, preferably $\geq$ about 1.25, and more preferably $\geq$ 1 5; and $DOS_S \geq$ about 0.2, and preferably $\geq$ about 0.25.

In another embodiment, the inventive $CA_{lk}S$ polymers having the following ratio of $DOS_{Alk}/DOS_S$ also provide concentration enhancement of low-solubility drugs:

$DOS_{Alk}/DOS_S <$ about 7, preferably $<$ about 6, and more preferably $<$ about 5.

The inventors have further found that $MCA_{lk}S$ polymers having the following DOS provide concentration enhancement of low-solubility drugs when used to formulate pharmaceutical compositions of such drugs:

$DOS_{M+Alk} \geq$ about 1.0, preferably $\geq$ about 1 25, and more preferably $\geq$ about 1.5; and $DOS_S \geq$ about 0.2, preferably $\geq$ about 0.25.

In another embodiment, the inventive $MCA_{lk}S$ polymers having the following ratio of $DOS_{M+Alk}/DOS_S$ also provide concentration enhancement of low-solubility drugs:

$DOS_{M+Alk}/DOS_S <$ about 7, preferably $<$ about 6 and more preferably $<$ about 5.

In general, and without wishing to be bound by any particular theory, it is believed that a principal reason the $CA_{lk}S/MCA_{lk}S$ polymers of the invention provide concentration enhancement of low-solubility drugs is that they are amphiphilic, containing relatively large amounts of both hydrophobic and hydrophilic groups. More specifically, in comparison to commercially available CAS, the addition of more acetyl and succinyl substituents results in more hydrophobic regions on the polymer, resulting in more surface area to associate with a low-solubility and/or hydrophobic drug, which in turn leads to improved concentration enhancement. It is believed this combination of hydrophobic and hydrophilic groups leads to improved concentration enhancement relative to commercial grades of CAS.

The inventors have also discovered that solid amorphous dispersions of hydrophobic drugs and $CA_{lk}S/MCA_{lk}S$ with improved physical stability can be obtained by reducing the difference in the solubility parameter between the drug and the polymer, as described herein.

Synthesis of Polymers

Methods for synthesis of substituted cellulosics are well known in the art. See, for example, U.S. Pat. No. 4,226,981 and Kelmm et al., *Comprehensive Cellulose Chemistry*, pages 164-197 and 207-249 (1998), the teachings of which are incorporated herein by reference.

HPMCAP and HPMCAT may be synthesized by treating HPMC with acetic anhydride and phthalic/trimellitic anhydride, as set forth herein. For hydroxypropyl methyl cellulose propionate phthalate (HPMCPrP) and hydroxypropyl methyl cellulose butyrate phthalate (HPMCBuP), propionic anhydride and butyric anhydride are substituted for acetic anhydride, respectively. For hydroxypropyl methyl cellulose propionate trimellitate (HPMCPrT) and hydroxypropyl methyl cellulose butyrate trimellitate (HPMCBuT), propionic anhydride and butyric anhydride are substituted for acetic anhydride, respectively.

Sources for HPMC include Dow Chemical Co. (Midland, Mich.), Shin-Etsu (Tokyo, Japan), Ashland Chemical Co. (Columbus, Ohio), Aqualon Inc. (Wilmington, Del.), and Colorcon Inc. (West Point, Pa.). A variety of HPMC starting materials are available, with various $DOS_M$ and $DOS_{HP}$. One skilled in the art will realize that the choice of HPMC starting material will have an influence on the solubility parameter and other properties of the $HPMCA_{lk}P/CA_{lk}T$ generated therefrom. Preferably, the HPMC has a $DOS_M$ ranging from 1.10 to 2.12, more preferably from 1.76 to 2.12, a $DOS_{HP}$ ranging from 0.10 to 0.35, more preferably from 0.18 to 0.35. Preferably, the viscosity of a 2% (w/v) aqueous solution of the HPMC ranges from 2 to 120,000 mPa-sec, preferably from 2 to 60 mPa-sec, and more preferably from 2.4 to 3.6 mPa-sec. Examples of such polymers include the E3 Prem LV grade from Dow and the Pharmacoat Grade 603 type 2910 from Shin Etsu.

Alternatively, the HPMC may be synthesized from cellulose using methods well known in the art. For example, cellulose may be treated with sodium hydroxide to produce swollen alkali cellulose, and then treated with chloromethane and propylene oxide to produce HPMC. See Kelmm et al., supra. The HPMC starting material preferably has a molecular weight ranging from about 600 to about 60,000 daltons, preferably from about 3,000 to about 50,000 daltons, and most preferably from about 6,000 to about 30,000 daltons.

$HPMCA_{lk}P/CA_{lk}T$ may also be synthesized by treating hypromellose phthalate (also known as hydroxypropyl methylcellulose phthalate or HPMCP) or hydroxypropyl methyl cellulose trimellitate (HPMCT).

$CA_{lk}S$ and $MCA_{lk}S$ may be synthesized from cellulose alkanate ($CA_{lk}$, that is, cellulose acetate, cellulose propionate, and cellulose butyrate) and methyl cellulose (MC), respectively, as described herein. Sources for $CA_{lk}$ include Eastman Chemical Co. (Kingsport, Tenn.). Sources for MC include Dow Chemical Co. (Midland, Mich.), Shin-Etsu (Tokyo, Japan), and Colorcon Inc. (West Point, Pa.). A variety of $CA_{lk}$ and MC grades are available, with various $DOS_{Alk}$ and $DOS_M$. One skilled in the art will recognize that the choice of $CA_{lk}$ and MC starting material will affect the solubility parameter and other properties of the $CA_{lk}S/MCA_{lk}S$ generated therefrom. In a preferred embodiment, the $CA_{lk}$ and MC starting material has a $DOS_{Alk}$ or a $DOS_M$ (for MC) ranging from about 1.5 to about 1.9. An example of such a $CA_{lk}$ polymer is the CA-320s polymer available from Eastman, while an example of such an MC polymer is Metalose SM-4 from Shin-Etsu. Alternatively, the $CA_R$, and MC may be synthesized from cellulose using methods well known in the art. The $CA_{lk}$ and MC starting materials preferably have a molecular weight ranging from about 600 to about 60,000 daltons, more preferably from about 3,000 to about 50,000 daltons, and most preferably from about 6,000 to from about 30,000 daltons.

Estenfication of HPMC, $CA_{lk}$, and MC to form HPMCAP, HPMCAT, CAS, and MCAS and the propionate- and butyrate-containing homologs may be carried out by one of two procedures. In a first procedure, the starting material is first dispersed or dissolved in a carboxylic acid solvent. For esterification with an acetate group, glacial acetic acid is preferred; for esterification with a propionate group, propionic acid is preferred; while for esterification with a butyrate group, butyric acid is preferred. The carboxylic acid solvent may be heated to promote dissolution of the HPMC therein Temperatures ranging from about 50 to about 120° C. may be used, with a temperature of about 85° C. preferred. Preferably the starting material is dissolved in the solvent; however, the starting material may only be dispersed in the solvent and formation of the substituted polymer with acceptable properties may still be obtained.

Depending upon which alkanyl group is to be included, an alkali carboxylate, which acts as an esterification catalyst, is included in the mixture of the carboxylic acid and HPMC. Exemplary alkali carboxylates include sodium and potassium acetate when the alkanyl group is acetyl; sodium and potassium propionate when the alkanyl group is propionyl; or sodium and potassium butyrate when the alkanyl group is butyryl. The concentration of alkali carboxylate generally ranges from about 1 to about 20 wt %, preferably from about 5 to about 20 wt % of the reaction mixture. Generally, the concentration of HPMC in the reaction mixture is about 1 to about 50 wt %, preferably about 5 to about 30 wt %.

Once the reaction mixture has been prepared, to obtain, e.g., HPMCAP, phthalic anhydride and acetic anhydride are added to begin the esterification reaction; for HPMCAT, acetic anhydride and trimellitic anhydride are added; for CAS and MCAS, succinic anhydride and acetic anhydride are added. The two reactants may be added into the reaction vessel simultaneously or consecutively. Alternatively, a portion of one of the reactants may be added to the reaction vessel first, followed by a portion of the second reactant; this process may be repeated until all of the desired amount of each reactant has been added. One skilled in the art will recognize that amount of each reactant added is determined by the desired degree of esterification desired in the final product. Typically, an excess of each reactant is used, usually from 1.0 to 5.0 times the stoichiometric amounts, although excess reactant of 10 times, 50 times, and as much as 100 times the stoichiometric amounts may also be used.

Once the esterification reaction is complete (generally, in from about 4 to 24 hours), a large volume of water is added to the reaction mixture (or vice-versa) and the pH is lowered to acidify the mixture and protonate the polymer to cause it to precipitated. In their protonated forms, $HPMCA_{lk}P/CA_{lk}T$ and $CA_{lk}S/MCA_{lk}S$ polymers are insoluble in water. As long as no base is added, the added water remains acidic and the polymer remains insoluble. The precipitated product is then subjected to thorough washing with water to remove impurities, and then dried. Optionally, the precipitated product may be dissolved in an organic solvent, such as acetone, re-precipitated in water, and then rinsed in water, followed by drying.

In a second procedure for forming the HPMCAP/CAT and CAS/MCAS polymers of the present invention, and the propionate- and butyrate-containing homologs, the starting material is dispersed or dissolved in an organic solvent, such as pyridine, acetone or dimethylformamide, along with a basic catalyst, such as pyridine or α-picoline; when pyridine is chosen as the solvent, it also functions as a catalyst for the synthesis. The concentration of starting material in the reaction mixture ranges from about 1 to about 70 wt %, preferably from about 5 to about 50 wt %. The phthalic/trimellitic/ succinic anhydride and acetic (or propionic or butyric) anhydride are then added as described above, and the reaction mixture heated to a temperature of from about 40° C. to about 120° C. for a period of from about 2 to about 120 hours to complete the esterification reaction. After completion of the esterification reaction, a large volume of 5-15 wt % sulfuric acid or hydrochloric acid is added to the reaction mixture to acidify the mixture and protonate the polymer so as to cause precipitation. The polymer is then purified by washing it with water and drying it.

The resulting polymer generally has a molecular weight that is about 1.7-fold that of the starting materials. Thus, the polymers of the present invention preferably have a molecular weight ranging from about 1,000 to about 100,000 daltons, preferably about 5,000 to about 80,000 daltons, and most preferably about 10,000 to about 50,000 daltons.

By commercial convention, the weight percent (wt %) of hydroxypropoxy, methoxy, acetyl, phthalyl, trimellityl, and succinyl groups are reported based on the mass of each of those groups attached to the saccharide group. Notwithstanding this convention, it has been discovered that the DOS on the cellulose backbone provides a more meaningful parameter for determining the effectiveness of a given grade of polymer for use in pharmaceutical compositions. This is because when the DOS of one substituent of the polymer is changed, the DOS of the other substituents stays the same. In contrast, a change in the wt % of one substituent results in a change in the wt % of all other substituents of the polymer, even if the DOS is not changed; this is because wt % is based on the total weight of the cellulose repeat unit, including all substituents. The DOS of hydroxypropoxy, methoxy, alkanyl and phthalyl/trimellityl/succinyl groups on the polymers of the invention can be determined from the wt % of the substituent on the polymer, which in turn can be calculated using known methods. See for example, U.S. Pat. No. 4,226,981 and *Japanese Pharmaceutical Excipients*, pages 182-187 (1893), the disclosures of which are incorporated herein by reference.

Rashan et al. disclose in 86 *J. AOAC Int'l.* 694 (2003) a procedure for determining the wt % of hydroxypropoxy and methoxy groups on HPMCAS which, by analogy, may be used to calculate the wt % of hydroxypropoxy and methoxy groups on HPMCA$_{lk}$P/CA$_{lk}$T polymers, and the wt % of methoxy groups on MCA$_{lk}$S. Using the method reported by Rashan et al., a 60-70 mg sample of the polymer is weighed into a vial. To this same vial are added 70-130 mg of adipic acid and a 2-mL portion of 57 wt % hydriodic acid in water. A 2-mL portion of o-xylene is then added into the vial and the vial capped and weighed. The vial is then heated to 150° C. and periodically shaken. After 1 hour of heating, the vial is allowed to cool to ambient temperature, which causes a phase separation into an upper o-xylene layer and a lower aqueous layer. About 1.5 mL of the o-xylene layer is removed using a pipette and placed into a small glass vial without disturbing the aqueous layer. Next, 1 mL of the removed o-xylene layer is measured into a 10-mL volumetric flask, diluted to volume with methanol, and mixed well. This is labeled as the Test Sample.

Standard solutions are prepared as follows. Approximately 2 mL o-xylene are placed into a 10-mL volumetric flask. Approximately 200 μL of iodomethane are then added to the flask and the weight of iodomethane added is recorded. Approximately 34 μL of 2-iodopropane are then added to the flask and the weight of iodopropane added is recorded. O-xylene is then added to the flask to bring the volume to 10 mL and the contents are well mixed. Next, 80-90 mg adipic acid are added to an 8-mL vial. To this same vial are added 2 mL of 57 wt % hydriodic acid and the vial is shaken. About 1.5 mL of the top o-xylene layer is removed using a pipette and placed in a small glass vial. Next, 1-mL of the removed α-xylene layer is measured into a 10-mL volumetric flask, diluted to the 10-mL volume with methanol, and mixed well. This is labeled as the Standard.

The Test Sample and Standard are analyzed by High Performance Liquid Chromatography (HPLC) as follows. Mobile Phase A consists of 90/10 v/v water/methanol and Mobile Phase B consists of 15/85 v/v water/methanol. A 10-μL volume of each of the Test Sample and the Standard is separately injected into an high performance liquid chromatograph. The chromatograph is equipped with an AQUA-SIL® column (5 μm, C$_{18}$ 125 Å, 150×4.60 mm). The flow rate is 1.0 mL/min with the following gradient profile from 0 to 8 min, 70% Mobile Phase A, 30% Mobile Phase B; from 8 to 10 min, 40% A, 60% B; from 10 to 17 min, 15% A, 85% B; and after 17 min, 15% A, 85% B; and at 17.01 min, 70% A, 30% B. Detection is by UV at a wavelength of 254 nm.

To calculate the amount of hydroxypropoxy and methoxy groups on the polymer sample, the standard response factor (RF$_i$) for species i based on the results with the Standard is calculated from the following equation:

$$RF_i = \frac{A_{std,i} * DF_{std,i} * V_{std,i}}{W_{std,i} * PF_i}$$

where A$_{std,i}$ is the peak area obtained for species i, DF$_{std,i}$ is the dilution factor for species i, V$_{std,i}$ is the volume of o-xylene used for preparing the standard, W$_{std,i}$ is the weight, in mg, of species i used for preparing the standard, and PF$_i$ is the purity factor for species i. RF$_i$ is calculated for both iodomethane and for 2-Iodopropane.

The amount of species i in the Test Sample is calculated from the following equation:

$$W_i = \frac{A_i * DF_i * V_i}{RF_i}$$

where the variables have the same definitions as above except that the values are for the Test Solution rather than for the Standard. The amount of both iodomethane and 2-Iodopropane are calculated in this manner.

The wt % of methoxy groups in the polymer is then calculated by the following equation:

$$\text{Methoxy(wt \%)} = 100 \times \frac{31.03}{141.94} \times \frac{W_{iodomethane}}{\text{weight of polymer}}$$

where W$_{iodomethane}$ is given by the above equation.

Similarly, the wt % of hydroxypropoxy groups in the polymer is calculated by the following equation:

$$\text{Hydroxypropoxy(wt \%)} = 100 \times \frac{75.09}{169.99} \times \frac{W_{2\text{-}iodopropane}}{\text{weight of polymer}}$$

where W$_{2\text{-}iodopropane}$ is given by the above equation.

Another procedure for determining the wt % of hydroxypropoxy and methoxy groups on a substituted cellulosic polymer is as set forth in *Japanese Pharmaceutical Excipients*, pages 182-187 (1993).

The weight percentage of acetyl, propionyl, butyryl, trimellityl, phthalyl, and succinyl groups on the polymers of the invention may be determined by an HPLC procedure as follows. Taking HPMCAP as an example, a 12.4-mg sample of the HPMCAP is placed into a glass sample solution vial. To the vial 4 mL of 1.0 N NaOH is added to hydrolyze the polymer by stirring for 4 hours using a magnetic stirrer. Then 4 mL of 1.2 M $H_3PO_4$ solution is added to lower the sample solution pH to less than 3. The sample solution vial is inverted several times to ensure complete mixing of the sample solution. The sample solution is then filtered through a 0.22-μm syringe filter into an HPLC vial prior to analysis.

As a control, a non-hydrolyzed HPMCAP sample is prepared by first weighing out 102.4 mg of the polymer into a control solution vial. To the vial, 4 mL of 20 mM $KH_2PO_4$ solution adjusted to pH 7.5 by the drop-wise addition of 1.0 N sodium hydroxide are added to dissolve the polymer by stirring for 2 hours using a magnetic stirrer. Then, 4 mL of 25 mM $H_3PO_4$ solution is added to precipitate the polymer. The control solution vial is inverted several times to ensure complete mixing. The control solution is then filtered through a 0 22-μm syringe filter into an HPLC vial prior to analysis.

The sample solution and control solution are analyzed by HPLC using a Phenomenex AQUA® 5μ C18 column (without a guard column) with sample detection at 215 nm and a sample size of 10 μl. The mobile phase is 20 mM $KH_2PO_4$ at pH 2 8 at a flow rate of 1.00 mL/min at ambient temperature. A series of standards of acetic acid and phthalic acid are prepared for calibration. From the HPLC analysis, the concentrations of acetic acid and phthalic acid in the sample solution and control solution are determined.

The acetyl and phthalyl contents of the HPMCAP are calculated from the measured acetic and phthalic acids in the hydrolyzed sample solution and the measured free acetic and phthalic acids in the non-hydrolyzed control solutions. The formulae used for calculations are as follows:

$$\text{Free Acetic Acid(wt \%)} = 100 \times \frac{[\text{Acetic Acid}]_{free}(\text{mg/mL})}{[\text{Polymer}]_{free}(\text{mg/mL})},$$

and $$\text{Free Phthalic Acid(wt \%)} = 100 \times \frac{[\text{Phthalic Acid}]_{free}(\text{mg/mL})}{[\text{Polymer}]_{free}(\text{mg/mL})},$$

where $[\text{Acetic Acid}]_{free}$ and $[\text{Phthalic Acid}]_{free}$ are the concentrations of free acetic and free phthalic acids in the non-hydrolyzed control solutions, respectively; and $[\text{Polymer}]_{free}$ is the concentration of the initially added HPMCAP in the non-hydrolyzed control solution. All concentrations are expressed in mg/mL.

The acetyl and phthalyl content of the HPMCAP is determined by the following formulae:

$$\text{Acetyl(wt \%)} = 100 \times \frac{43.04}{60.05} \times \frac{([\text{Acetic Acid}]_{Hyd} - [\text{Acetic Acid}]_{free} \times [\text{Polymer}]_{Hyd}/[\text{Polymer}]_{free})(\text{mg/mL})}{[\text{Polymer}]_{Hyd}(\text{mg/mL})},$$

and $$\text{Phthalyl(wt \%)} = 100 \times \frac{101.08}{118.09} \times \frac{([\text{Phthalic Acid}]_{Hyd} - [\text{Phthalic Acid}]_{free} \times [\text{Polymer}]_{Hyd}/[\text{Polymer}]_{free})(\text{mg/mL})}{[\text{Polymer}]_{Hyd}(\text{mg/mL})},$$

where $[\text{Acetic Acid}]_{Hyd}$ and $[\text{Phthalic Acid}]_{Hyd}$ are the concentrations of acetic and phthalic acids in the hydrolyzed sample solution, respectively; $[\text{Acetic Acid}]_{free}$ and $[\text{Phthalic Acid}]_{free}$ are the concentrations of free acetic and phthalic acids in the non-hydrolyzed control solutions, respectively; and $[\text{Polymer}]_{free}$ and $[\text{Polymer}]_{Hyd}$ are the concentrations of the initially added HPMCAP polymer in the non-hydrolyzed control solution and in the hydrolyzed sample solution, respectively All concentrations are expressed in mg/mL.

The foregoing methods may be used in an analogous manner to measure wt % of propionyl, butyryl, trimellityl, and succinyl groups by simply substituting where appropriate propionic or butyric acid for acetic acid and trimellitic acid or succinic acid for phthalic acid, and adjusting for the molecular weight of these substituents in the appropriate formulae. This information may then be used to calculate the DOS for each substituent on the polymer using the following procedure.

First, the wt % of the $HPMCA_{Ik}P/CA_{Ik}T$ that is the backbone, i.e., the fraction of the polymer that is not substituted is determined by the following equation, taking HPMCAP as an example. Backbone(wt %)=100−methoxy(wt %)−hydroxypropoxy(wt %)−acetyl(wt %)−phthalyl(wt %) Next, the number of moles of backbone per 100 g of polymer, $M_{backbone}$ is estimated from the following equation:

$$M_{backbone} = \frac{(\text{Backbone(wt \%)} + (\text{methoxy(wt \%)} + \text{hydroxypropoxy(wt \%)}) \times 16)}{159}$$

This equation accounts for the fact that the wt % for methoxy and hydroxypropoxy groups includes the oxygen that was part of the hydroxyl group on the saccharide repeat unit, while the wt % for acetyl and phthalyl groups do not. One skilled in the art will appreciate that the above equation will yield only an approximate number of moles of backbone per 100 g of polymer; an iterative calculation is required to determine the actual number of moles. However, the inventors have found that this approximation greatly reduces the number of calculations required to determine the DOS, and results in a calculated DOS that is within the error range for measurements of the wt % of substituents on the polymers of the invention. The DOS specified herein for the polymers of the invention is calculated using this approximation.

The DOS of the various substituents for the polymers of the invention is then determined by dividing the number of moles of the substituent (calculated by dividing the wt % of the substituent by the molecular weight of the substituent) by the number of moles of the backbone. Taking HPMCAP as an example, the DOS calculations would be as follows:

$$DOS_M = \frac{\text{methoxy(wt \%)}/31.03}{M_{backbone}},$$

$$DOS_{HP} = \frac{\text{hydroxypropoxy(wt \%)}/75.09}{M_{backbone}},$$

$$DOS_{Ac} = \frac{\text{acetyl(wt \%)}/43.04}{M_{backbone}},$$

and $$DOS_P = \frac{\text{phthalyl(wt \%)}/149.12}{M_{backbone}}.$$

The DOS for trimellitate, succinate, propionate, and butyrate groups is calculated using the same procedure, except that the following equations are used for these groups.

$$DOS_T = \frac{\text{trimellityl(wt \%)}/192.13}{M_{backbone}},$$

$$DOS_S = \frac{\text{succinyl(wt \%)}/101.08}{M_{backbone}}.$$

$$DOS_{Pr} = \frac{\text{propionyl(wt \%)}/57.08}{M_{backbone}},$$

and $$DOS_{Bu} = \frac{\text{butyryl(wt \%)}/71.11}{M_{backbone}}.$$

Low-Solubility Drugs

The term "drug" is conventional, denoting a compound having beneficial prophylactic and/or therapeutic properties when administered to an animal, especially humans. Preferably, the drug is a "low-solubility drug," meaning that the drug has a minimum aqueous solubility at physiologically relevant pH (e.g., pH 1-8) of about 0.5 mg/mL or less. The invention finds greater utility as the aqueous solubility of the drug decreases. Thus, compositions of the present invention are preferred for low-solubility drugs having an aqueous solubility of less than about 0.2 mg/mL, more preferred for low-solubility drugs having an aqueous solubility of less than about 0.1 mg/mL, more preferred for low-solubility drugs having an aqueous solubility of less than about 0.05 mg/mL, and even more preferred for low-solubility drugs having an aqueous solubility of less than about 0.01 mg/mL. Preferably, the drug has a minimum aqueous solubility over the pH range of 6.5 to 7.5 of about 0.5 mg/mL or less, more preferably less than about 0.2 mg/mL, even more preferably less than about 0.1 mg/mL, still more preferably less than about 0.05 mg/mL, and most preferably less than about 0.01 mg/mL. In general, it may be said that the drug has a dose-to-aqueous solubility ratio greater than about 10 mL, and more typically greater than about 100 mL, where the aqueous solubility (mg/mL) is the minimum value observed in any physiologically relevant aqueous solution (e.g., those with pH values between 1 and 8) including USP simulated gastric and intestinal buffers, and dose is in mg. Thus, a dose-to-aqueous solubility ratio may be calculated by dividing the dose (in mg) by the aqueous solubility (in mg/mL).

Although low-solubility drugs represent a preferred class for use with the invention, the drug does not need to be a low-solubility drug in order to benefit from the invention. Even a drug that exhibits appreciable aqueous solubility in the environment of use can benefit from the enhanced aqueous concentration and improved bioavailability made possible by the invention if it reduces the size of the dose needed for therapeutic efficacy or increases the rate of drug absorption in cases where a rapid onset of the drug's effectiveness is desired. In such cases, the drug may have an aqueous solubility up to about 1 to 2 mg/mL, or even as high as about 20 to 40 mg/mL.

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, triglyceride-reducing agents, anti-atherosclerotic agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesteryl ester transfer protein inhibitors.

Each named drug should be understood to include any pharmaceutically acceptable forms of the drug. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs.

Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, delayerdine and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4',6'-trimethylphenoxy)pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, levocetirizine, decarboethoxyloratadine and cinnarizine; specific examples of antipsychotics include ziprasidone, olanzepine, thiothixene hydrochloride, fluspirilene, risperidone and penfluridol; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalapnlic acid, quinapril and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R—(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl+3-oxypropyl]amide; and specific examples of cholesteryl ester transfer protein (CETP) inhibitors include [2R,4S) 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib), (2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester, (2R)-3-[[3-(4-chloro-3-ethylphenoxy)phenyl][[3-(1,1,2,2-tetrafluoroethoxy)phenyl]methyl]amino]-1,1,1-trifluoro-2-propanol, (2R,4R,4aS)-4-(amino-(3,5-bis-(trifluoromethyl-phenyl)-methyl]-2-ethyl-6-(trifluoromethyl)-3,4-dihydroquinoline-1-carboxylic acid isopropyl ester, S-[2-([[1-(2-ethylbutyl)cyclohexyl]carbonyl]amino)phenyl]2-methylpropanethioate, trans-4-[[[2-[[[[3,5-bis(trifluoromethyl)phenyl]methyl](2-methyl-2H-tetrazol-5-yl)amino]methyl]-4-(trifluoromethyl)phenyl]ethylamino]methyl]-cyclohexaneacetic acid, trans-4-[[[2-[[[[3,5-bis(trifluoromethyl)phenyl]methyl](2-methyl-2H-tetrazol-5-yl)amino]methyl]-5-methyl-4-(trifluoromethyl)phenyl]ethylamino]methyl]-cyclohexaneacetic acid, the drugs disclosed in commonly owned U.S. patent application Ser. Nos. 09/918,127 and 10/066,091, the disclosures of both of which are incorporated herein by reference, and the drugs disclosed in the following patents and published applications, the disclosures of all of which are incorporated herein by reference: DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; WO 9835937 A1; JP 11049743; WO 0018721; WO 0018723; WO 0018724; WO 0017164; WO 0017165; WO 0017166; WO 04020393; EP 992496; and EP 987251.

Rather surprisingly and in contrast to conventional wisdom, the relative degree of enhancement in aqueous concentration and bioavailability provided by the compositions of the present invention generally improves for drugs as solubility decreases and hydrophobicity increases. In fact, the inventors have recognized a subclass of hydrophobic drugs that are essentially aqueous-insoluble, highly hydrophobic, and are characterized by a set of physical properties. This subclass, referred to herein as "hydrophobic drugs," exhibits dramatic enhancements in aqueous concentration and bioavailability when formulated using the polymers of the present invention.

The first and most obvious property of hydrophobic drugs is that they are extremely hydrophobic. Log P, defined as the base 10 logarithm of the ratio of the drug solubility in octanol to the drug solubility in water, is a widely accepted measure of hydrophobicity. By "extremely hydrophobic" is meant that the Log P value of the drug preferably is ≥4.0, more preferably >5.0, and most preferably ≥5.5. Log P may be measured experimentally or calculated using methods known in the art. When using a calculated value for Log P, the highest value calculated using any generally accepted method for calculating Log P is used. Calculated Log P values are often referred to by the calculation method, such as Clog P, Alog P, and Mlog P. The Log P may also be estimated using fragmentation methods, such as Crippen's fragmentation method (27 *J. Chem. Inf. Comput. Sci.* 21 (1987)); Viswanadhan's fragmentation method (29 *J. Chem Inf. Comput. Sci.* 163 (1989)); or Broto's fragmentation method (19 *Eur. J. Med. Chem.-Chim. Theor.* 71 (1984). Preferably the Log P value is calculated by using the average value estimated using Crippen's, Viswanadhan's, and Broto's fragmentation methods. The second property of hydrophobic drugs is that they have a low solubility parameter, as calculated using the methods described herein. The solubility parameter for hydrophobic drugs is typically ≤about 22 $(J/cm^3)^{1/2}$, preferably ≤about 21.5 $(J/cm^3)^{1/2}$, and more preferably ≤about 21 $(J/cm^3)^{1/2}$.

Primarily as a consequence of these properties, hydrophobic drugs typically have an extremely low aqueous solubility. By "extremely low aqueous solubility" is meant that the minimum aqueous solubility at a physiologically relevant pH of 1 to 8 is less than about 100 μg/mL and often less than about 10 μg/mL. In addition, hydrophobic drugs often have a very high dose-to-solubility ratio. Extremely low aqueous solubility often leads to poor or slow absorption of the drug from the fluid of the gastrointestinal tract, when the drug is dosed orally in a conventional manner. For extremely low-solubility drugs, absorption generally becomes progressively more difficult as the dose (mass of drug given orally) increases. Thus, a second property of hydrophobic drugs is a very high dose (in mg) to solubility (in mg/mL) ratio. By "very high dose-to-solubility ratio" is meant that the dose-to-solubility ratio has a value of ≥about 1000 mL, preferably ≥about 5,000 mL, or and more preferably ≥about 10,000 mL.

Hydrophobic drugs also typically have very low absolute bioavailabilities. Specifically, the absolute bioavailability of drugs in this subclass when dosed orally in their unformulated state (i.e., drug alone) is less than about 10% and more often less than about 5%.

One class of hydrophobic drugs that works well in compositions comprising the polymers of the present invention is cholesteryl ester transfer protein (CETP) inhibitors. Solid amorphous dispersions of CETP inhibitors and the polymers of the present invention show dramatic improvements in bioavailability and concentration enhancement in both in vitro and in vivo tests relative to crystalline drug alone.

Compositions comprising the polymers of the present invention and CETP inhibitors may be used in combination with 3-hydroxy-3-methylglutaryl-coenzyme A (HMG-CoA) reductase inhibitors. In one embodiment, a unitary dosage form comprises (1) a solid amorphous dispersion of a CETP inhibitor and a polymer of the present invention and (2) an HMG-CoA reductase inhibitor. In a preferred embodiment, the HMG-CoA reductase inhibitor is from a class of therapeutics commonly known as statins. Preferably the HMG-CoA reductase inhibitor is selected from the group consisting of fluvastatin, lovastatin, pravastatin, atorvastatin, simvastatin, cerivastatin, rivastatin, mevastatin, velostatin, compactin, dalvastatin, fluindostatin, rosuvastatin, pitivastatin, dihydrocompactin, and pharmaceutically acceptable forms thereof. By "pharmaceutically acceptable forms" is meant any pharmaceutically acceptable derivative or variation, including stereoisomers, stereoisomer mixtures, enantiomers, solvates, hydrates, isomorphs, polymorphs, salt forms and prodrugs. In one embodiment, the HMG-CoA reductase inhibitor is selected from the group consisting of atorvastatin, fluvastatin, lovastatin, pravastatin, simvastatin, rosuvastatin, and pharmaceutically acceptable forms thereof. In another preferred embodiment, the HMG-CoA reductase inhibitor is selected from the group consisting of atorvastatin, the cyclized lactone form of atorvastatin, a 2-hydroxy, 3-hydroxy or 4-hydroxy derivative of such compounds, and pharmaceutically acceptable forms thereof. Even more preferably, the HMG-CoA reductase inhibitor is atorvastatin hemicalcium trihydrate. Further details of such dosage forms are provided in commonly owned U.S. patent application Ser. No. 10/739,567, filed Dec. 12, 2003, filed Dec. 20, 2002, the disclosure of which is incorporated herein by reference.

Solubility Parameters

Solubility parameters are a well known tool in the art used to correlate and predict cohesive and adhesive properties of materials. A complete discussion of solubility parameters is provided in Barton's *Handbook of Solubility Parameters and Other Cohesion Parameters* (1983), hereinafter referred to as "Barton", the disclosure of which is incorporated herein by reference.

While several methods can be used to determine the solubility parameter of a given compound, in this specification and in the claims, by "solubility parameter" is meant the Hildebrand solubility parameter calculated from group molar cohesive energy constants, as described herein and in Barton, pages 61-66. Hildebrand solubility parameters have units of $(J/cm^3)^{1/2}$. Specifically, the solubility parameter for compound i ($\delta_i$) is calculated from the equation $$\delta_i = \left[ \frac{-\sum_z U_z}{\sum_z V_z} \right]^{1/2},$$

where z represents a contributing group on compound i, $U_z$ is the molar vaporization energy (at 25° C.) of the contributing group, and $V_z$ is the molar volume (at 25° C.) of the contributing group. The following table gives group contributions to the molar vaporization energy and molar volume for various groups. Thus, when the chemical structure of a compound is known, its solubility parameter can be calculated using the foregoing equation and the group contributions given in the following table.

| Group Contributions to the Molar Vaporization Energy and Molar Volume at 25° C. | | |
|---|---|---|
| Group, Z | $-U_z$ (kJ/mol) | $V_z$ (cm³/mol) |
| —CH₃ | 4.71 | 33.5 |
| —CH₂— | 4.94 | 16.1 |
| \CH— / | 3.43 | −1.0 |
| \CH/ /\ | 1.47 | −19.2 |
| H₂C= | 4.31 | 28.5 |
| —CH= | 4.31 | 13.5 |
| \C= / | 4.31 | −5.5 |
| HC≡ | 3.85 | 27.4 |
| —C≡ | 7.07 | 6.5 |
| Phenyl | 31.9 | 71.4 |
| Phenylene (o, m, p) | 31.9 | 52.4 |
| Phenyl (trisubstituted) | 31.9 | 33.4 |
| Phenyl (tetrasubstituted) | 31.9 | 14.4 |
| Phenyl (pentasubstituted) | 31.9 | −4.6 |
| Phenyl (hexasubstituted) | 31.9 | −23.6 |
| Ring closure, 5 or more atoms | 1.05 | 16 |
| Ring closure, 3 or 4 atoms | 3.14 | 18 |
| Conjugation in ring, for each double bond | 1.67 | −2.12 |
| Halogen attached to C atom with double bond | −20% of halogen $U_z$ | |
| —F | 4.19 | 18.0 |
| —F (disubstituted) | 3.56 | 20.0 |
| —F (trisubstituted) | 2.30 | 22.0 |
| —CF₂ | 3.28 | 23.1 |
| —CF₂ (for perfluoro compounds) | 4.27 | 23.0 |
| —CF₃ | 8.09 | 54.8 |
| —CF₃ (for perfluoro compounds | 4.27 | 57.5 |
| —Cl | 11.55 | 24.0 |
| —Cl (disubstituted) | 9.63 | 26.0 |
| —Cl (trisubstituted) | 7.53 | 27.3 |
| —Br | 15.49 | 30.0 |
| —Br (disubstituted) | 12.4 | 31.0 |
| —Br (trisubstituted) | 10.7 | 32.4 |
| —I | 19.05 | 31.5 |
| —I (disubstituted) | 16.7 | 33.5 |
| —I (trisubstituted) | 16.3 | 37.0 |
| —CN | 25.5 | 24.0 |
| —OH | 29.8 | 10.0 |
| —OH (disubstituted or on adjacent C atoms) | 21.9 | 13.0 |
| —O— | 3.35 | 3.8 |
| —CHO (aldehyde) | 21.4 | 22.3 |
| —CO— | 17.4 | 10.8 |
| —CO₂— | 18.0 | 18.0 |
| —CO₃— (carbonate) | 17.6 | 22.0 |

Group Contributions to the Molar Vaporization Energy and Molar Volume at 25° C.

| Group, Z | $-U_z$ (kJ/mol) | $V_z$ (cm³/mol) |
|---|---|---|
| —C₂O₃— (anhydride) | 30.6 | 30.0 |
| HCOO— (formate) | 18.0 | 32.5 |
| —CO₂CO₂— (oxalate) | 26.8 | 37.3 |
| —NNH₂ | 16.7 | 16 |
| —NHNH— | 16.7 | 16 |
| —N₂(diazo) | 8.4 | 23 |
| —N=N— | 4.2 | — |
| \C=N—N=C/ | 20.1 | 0 |
| —N=C=N— | 11.47 | — |
| —NC | 18.8 | 23.1 |
| —NF₂ | 7.66 | 33.1 |
| —NF— | 5.07 | 24.5 |
| —CONH₂ | 41.9 | 17.5 |
| —CONH— | 33.5 | 9.5 |
| —CON\ | 29.5 | −7.7 |
| HCON\ | 27.6 | 11.3 |
| HCONH— | 44.0 | 27.0 |
| —NHCOO— | 26.4 | 18.5 |
| —NHCONH— | 50.2 | — |
| —NHCON\ | 41.9 | — |
| \NCON/ | 20.9 | −14.5 |
| NH₂COO— | 37.0 | — |
| —NCO | 28.5 | 35.0 |
| —ONH₂ | 19.1 | 20.0 |
| \C=NOH | 25.1 | 11.3 |
| —CH=NOH | 25.1 | 24.0 |
| —NO₂ (aliphatic) | 29.3 | 24.0 |
| —NO₂ (aromatic) | 15.36 | 32.0 |
| —NO₃ | 20.9 | 33.5 |
| —NO₂ (nitrite) | 11.7 | 33.5 |
| —NHNO₂ | 39.8 | 28.7 |
| —NNO | 27.2 | 10 |
| —SH | 14.44 | 28.0 |
| —S— | 14.15 | 12 |
| —S₂— | 23.9 | 23.0 |
| —S₃— | 13.40 | 47.2 |
| \SO/ | 39.1 | — |
| SO₃ | 18.8 | 27.6 |
| SO₄ | 28.5 | 31.6 |
| —SO₂Cl | 37.1 | 43.5 |
| —SCN | 20.1 | 37.0 |
| —NCS | 25.1 | 40.0 |
| P | 9.42 | −1.0 |
| PO₃ | 14.2 | 22.7 |
| PO₄ | 20.9 | 28.0 |
| PO₃(OH) | 31.8 | 32.2 |
| Si | 3.4 | 0 |
| SiO₄ | 21.8 | 20.0 |
| B | 13.8 | −2.0 |
| —HCO₃ | 12.6 | 18.0 |
| —COF | 13.4 | 29.0 |
| —COCl | 17.6 | 38.1 |
| COBr | 24.2 | 41.6 |
| COI | 29.3 | 48.7 |
| —NH₂ | 12.6 | 19.2 |
| —NH— | 8.4 | 4.5 |
| \N— / | 4.2 | −9.0 |
| —N= | 11.7 | 5.0 |
| —NHNH₂ | 22.0 | — |
| BO₃ | 0.0 | 20.4 |
| Al | 13.8 | −2.0 |
| Ga | 13.8 | −2.0 |
| In | 13.8 | −2.0 |
| Tl | 13.8 | −2.0 |
| Ge | 8.1 | −1.5 |
| Sn | 11.3 | 1.5 |
| Pb | 17.2 | 2.5 |
| As | 13.0 | 7.0 |
| Sb | 16.3 | 8.9 |

For example, the CETP inhibitor [2R,4S]-4[(3,5-bis-trifluoromethyl-benzyl)-methoxycarbonyl-amino]-2-ethyl-6-trifluoromethyl-3,4-dihydro-2H-quinoline-1-carboxylic acid ethyl ester, also known as torcetrapib (Drug 1 in the Examples), has the following chemical structure.

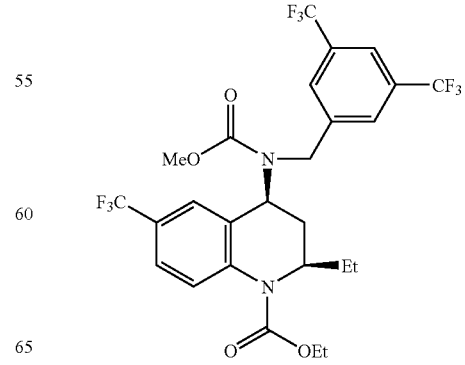

The group contributions for torcetrapib may be obtained from the above tables and are summarized in the following table.

| Group, z | Number of Groups | —$U_z$ (kJ/mol) | $V_z$ (cm³/mol) | $\Sigma$—$U_z$ (kJ/mol) | $\Sigma V_z$ (cm³/mol) |
|---|---|---|---|---|---|
| CH$_3$ | 3 | 4.71 | 33.5 | 14.1 | 100.5 |
| CH$_2$ | 4 | 4.94 | 16.1 | 19.8 | 64.4 |
| >CH— | 2 | 3.43 | −1 | 6.9 | −2 |
| Phenyl (trisubstituted) | 2 | 31.9 | 33.4 | 63.8 | 66.8 |
| Ring closure (5 or more atoms) | 1 | 1.05 | 16 | 1.1 | 16 |
| —O— | 2 | 3.35 | 3.8 | 6.7 | 7.6 |
| —CO— | 2 | 17.4 | 10.8 | 34.8 | 21.6 |
| >N— | 2 | 4.2 | −9 | 8.4 | −18 |
| —CF$_3$ | 3 | 8.09 | 54.8 | 24.3 | 164.4 |
| Total | | | | 179.8 | 421.3 |

These values can then be inserted into the above equation to calculate the solubility parameter for the drug torcetrapib, as shown below.

$$\delta_{torcetrapib} = \left[\frac{-\sum_z U_z}{\sum_z V_z}\right]^{1/2}$$

$$= \left[\frac{179.8 kJ/mol * 1000 J/kJ}{421.3 cm^3/mol}\right]^{1/2}$$

$$= 20.66 (J/cm^3)^{1/2}$$

For polymers, the average number of groups on each repeat unit is calculated, and the values of the group contributions are used to calculate the solubility parameter in the same fashion. For example, HPMCA$_{lk}$P has the following general structure.

cellulose polymer backbone, the solubility parameter of Polymer 1 is calculated as follows:

| Group, z | Number of Groups | —$U_z$ (kJ/mol) | $V_z$ (cm³/mol) | $\Sigma$—$U_z$ (kJ/mol) | $\Sigma V_2$ (cm³/mol) |
|---|---|---|---|---|---|
| CH3 | 2.70 | 4.71 | 33.5 | 12.7 | 90.5 |
| CH2 | 1.25 | 4.94 | 16.1 | 6.2 | 20.1 |
| >CH— | 5.25 | 3.43 | −1.0 | 18.0 | −5.3 |
| >C< | 0.00 | 1.47 | −19.2 | 0 | 0.0 |
| disub phenyl | 0.20 | 31.90 | 52.4 | 6.4 | 10.5 |
| ring closure (5 or more) | 1.00 | 1.05 | 16.0 | 1.1 | 16.0 |
| —OH | 0.35 | 30.00 | 10.0 | 10.4 | 3.5 |
| —O— | 4.13 | 3.35 | 3.8 | 13.8 | 15.7 |
| —CO— | 0.77 | 17.40 | 10.8 | 13.4 | 8.3 |
| COOH | 0.20 | 27.60 | 28.5 | 5.5 | 5.7 |
| Total | | | | 87.5 | 165.0 |

These values can then be inserted into the above equation for calculating solubility parameter, as follows:

$$\delta_{POLYMER1} = \left[\frac{-\sum_z U_z}{\sum_z V_z}\right]^{1/2}$$

$$= \left[\frac{87.5 kJ/mol * 1000 J/kJ}{165.0 cm^3/mol}\right]^{1/2}$$

$$= 23.0 (J/cm^3)^{1/2}$$

In this fashion, the solubility parameters of the polymers of the present invention can be calculated.

The inventors have discovered that for low-solubility drugs, and in particular, for hydrophobic drugs, the solubility of the amorphous form of a drug in a polymer of the invention is related to the difference between (1) the solubility param-

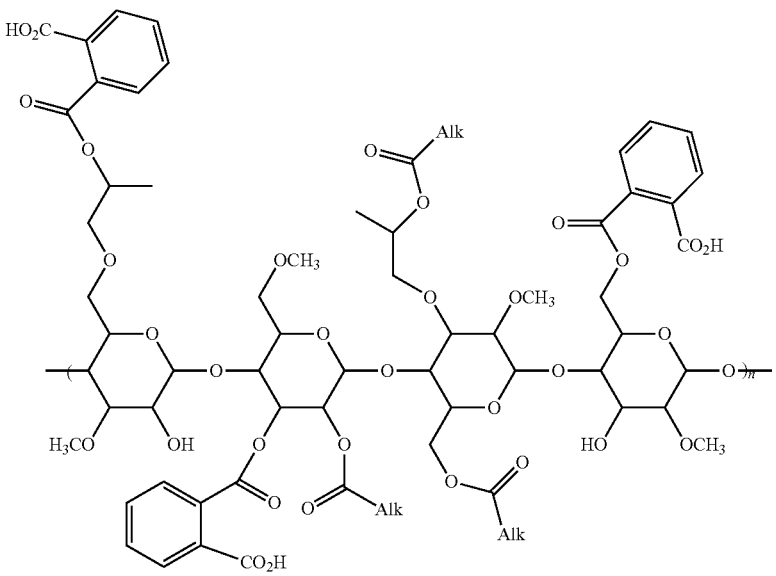

Polymer 1 in the Examples section below has the following DOS: 0.25 hydroxypropoxy, 1.88 methoxy, 0.57 acetyl, and 0.20 phthalyl. Using these DOS values and the structure of the eter of the drug and (2) the solubility parameter of the polymer. As this difference is decreased, the solubility of the drug in the polymer is increased. For solid amorphous dispersions, as the solubility of the drug in the polymer increases, the physical stability of the dispersion increases.

Thus, in one embodiment, for HPMCA$_{lk}$P/CA$_{lk}$T, the polymer has a solubility parameter of no greater than about 24.0 (J/cm$^3$)$^{1/2}$. Preferably, the HPMCA$_{lk}$P/CA$_{lk}$T polymer has a solubility parameter of no greater than about 23.8 (J/cm$^3$)$^{1/2}$, and more preferably, no greater than about 23.6 (J/cm$^3$)$^{1/2}$.

In another embodiment, for CA$_{lk}$S/MCA$_{lk}$S, the polymer has a solubility parameter of no greater than about 27.0 (J/cm$^3$)$^{1/2}$. Preferably, the CA$_{lk}$S/MCA$_{lk}$S polymer has a solubility parameter of no greater than about 26.5 (J/cm$^3$)$^{1/2}$, and more preferably no greater than about 26.0 (J/cm$^3$)$^{1/2}$.

Pharmaceutical Compositions

In one embodiment, the present invention provides a pharmaceutical composition comprising a low-solubility drug and a polymer of the present invention (HPMCA$_{lk}$P, HPMCA$_{lk}$T, CA$_{lk}$S, or MCA$_{lk}$S). The amount of polymer relative to the amount of drug present in the compositions of the present invention depends on the drug and combination of substituent levels on the polymer and may vary widely from a drug-to-polymer weight ratio of from 0.01 to about 100 (e.g., 1 wt % drug to 99 wt % drug). In most cases it is preferred that the drug-to-polymer ratio is greater than about 0.05 (4.8 wt % drug) and less than about 20 (95 wt % drug). Thus, the pharmaceutical composition may comprise at least about 5 wt % drug, at least about 10 wt % drug, at least about 25 wt % drug, at least about 30 wt % drug, at least about 40 wt % drug, at least about 50 wt % drug, at least about 60 wt % drug, at least about 70 wt % drug, at least about 80 wt % drug, and even at least about 90 wt % drug.

In a preferred embodiment, the composition has a high loading of drug. By "high loading of drug" is meant that the pharmaceutical composition comprises at least about 40 wt % drug. Preferably, the pharmaceutical composition comprises at least about 45 wt % drug, and more preferably at least about 50 wt % drug. Such high loadings of drug are desirable to keep the mass of the pharmaceutical composition at a low value.

The low-solubility drug and polymer may be combined in any manner. In one class of embodiments, the composition comprises a combination of a low-solubility drug and the polymer of the present invention. "Combination" as used herein means that the low-solubility drug and polymer may be in physical contact with each other or in close proximity but without necessarily being physically mixed. For example, the composition may be in the form of a multi-layer tablet, wherein one or more layers comprises the low-solubility drug and one or more different layers comprises a polymer of the invention. Or the composition may be in the form of a coated tablet wherein either the low-solubility drug or the polymer or both are present in the tablet core and the coating includes the low-solubility drug or the polymer or both. Alternatively, the composition can be in the form of a simple dry physical mixture wherein both the drug and polymer are mixed in particulate form and wherein the particles of each, regardless of size, retain the same individual physical properties that they exhibit in bulk.

Combinations of low-solubility drugs and the polymers of the invention may be formed in any conventional way such as by blending dry ingredients that include the low-solubility drug, the polymer, and any other excipients appropriate to forming the desired dosage form using V-blenders, planetary mixers, vortex blenders, mills, extruders such as twin-screw extruders, and trituration processes. The ingredients can be combined in granulation processes utilizing mechanical energy, such as ball mills or roller compactors. They may also be combined using wet granulation methods in high-shear granulators or fluid bed granulators wherein a solvent or wetting agent is added to the ingredients or the polymer may be dissolved in a solvent and used as a granulating fluid. The polymer may be added as a coating to tablets preformed by a compression process from a mixture containing a low-solubility drug, the coating taking place in a spray-coating process using, for example, a pan coater or a fluidized-bed coater.

Alternatively, the compositions of the present invention may be co-administered, meaning that the low-solubility drug can be administered separately from, but within the same general time frame as, the polymer. Thus, the low-solubility drug can, for example, be administered in its own dosage form that is taken at approximately the same time as the polymer that is in a separate dosage form. If administered separately, it is generally preferred to administer both the low-solubility drug and the polymer within 60 minutes of each other, so that the two are present together in the environment of use. When not administered simultaneously, the polymer is preferably administered prior to the low-solubility drug.

In a preferred embodiment, the low-solubility drug is intimately mixed with the polymer. As used herein, by "intimately mixed" or "intimate mixture" is meant that the low-solubility drug and polymer are in physical contact with each other or in close proximity to each other in the composition. For example, the low-solubility drug and the polymer may be dry or wet granulated using the methods noted above. Alternatively, the low-solubility drug and the polymer may be in the form of a solid amorphous dispersion, as described herein below. Alternatively, the low-solubility drug may be in the form of particles at least partially coated with the polymer. By "particles" is meant individual crystals of the drug when the drug is crystalline. When the drug is amorphous, "particles" refers to individual particles comprising drug in amorphous form. In general, the particles may range in size from about 0.1 μm to about 500 μm. By "at least partially coated" with the polymer means that the polymer partially coats at least a portion of the surface of the drug particles. The polymer may coat only a portion of the drug particle, or may fully coat or encapsulate the entire surface of the drug particle. Intimate mixtures of the low-solubility drug and the polymer are preferred because when the composition is administered to an aqueous use environment the drug and polymer can begin to dissolve together in close proximity, resulting in concentration enhancement and/or an improvement in bioavailability. This is in contrast to an enteric coated tablet consisting, for example, of a drug-containing core coated with a polymer, where the polymer may dissolve first in the use environment, followed by dissolution of the drug from the core. In such controlled release devices the polymer and drug may not dissolve together in close proximity and no enhancement in concentration or bioavailability may be obtained.

In a preferred embodiment, the composition comprises a combination of a low-solubility drug and the polymer, wherein the drug is in a solubility-improved form. By "solubility-improved form" is meant a form of the drug that provides a maximum dissolved drug concentration of the low-solubility drug that is at least about 1.1-fold, more preferably at least about 1 25-fold, even more preferably at least about 2.0-fold the equilibrium drug concentration provided by the crystalline form of the low-solubility drug alone (or the amorphous form if the crystalline form is unknown). Alternatively, the solubility-improved form provides an area under the drug concentration versus time curve (AUC) in the use environment that is at least about 1.1-fold, preferably at least 1.25- fold and more preferably at least 2.0-fold that provided by a control composition. The control composition is the lowest-energy or most stable crystalline form of the low-solubility drug alone, which is the low-solubility drug in solid bulk crystalline form (or the solid amorphous form if the crystalline form is unknown) and free from solubilizers or other components that would materially affect the drug's solubility. In one embodiment, the low-solubility drug in solubility-improved form is intimately mixed with the polymer.

The solubility-improved form of the low-solubility drug may comprise a solid amorphous dispersion of the drug in a concentration-enhancing polymer or in a low molecular weight water-soluble material, as described below. The solubility-improved form may also comprise a crystalline highly soluble form of the low-solubility drug such as a salt; a high-energy crystalline form of the low-solubility drug; a hydrate or solvate crystalline form of a low-solubility drug; an amorphous form of a low-solubility drug (for a low-solubility drug that may exist as either amorphous or crystalline); a mixture of the low-solubility drug (amorphous or crystalline) and a solubilizing agent, or a solution of the low-solubility drug dissolved in an aqueous or organic liquid. Such solubility-improved forms are disclosed in commonly assigned U.S. patent application Ser. No. 09/742,785, filed Dec. 20, 2000, the disclosure of which is incorporated herein by reference. The solubility-improved form may also comprise a solid adsorbate comprising a low-solubility drug adsorbed onto a substrate, the substrate having a surface area of at least 20 m$^2$/g, and wherein at least a major portion of the low-solubility drug in the solid adsorbate is amorphous, as disclosed in commonly assigned U.S. patent application Ser. No. 10/173,987, filed Jun. 17, 2002, the disclosure of which is incorporated herein by reference. The solubility-improved form may also comprise a low-solubility drug formulated in a self-emulsifying lipid vehicle of the type disclosed in commonly assigned U.S. patent application Ser. No. 10/175,643 filed Jun. 19, 2002, the disclosure of which is also incorporated herein by reference.

In a preferred embodiment, the low-solubility drug and polymer of the present invention are formed into a solid amorphous dispersion by any of the methods described herein. By "solid amorphous dispersion" is meant a solid material in which at least a portion of the low-solubility drug is in the amorphous form and dispersed in the polymer. In this embodiment, it is preferred that the polymer be water soluble or water dispersible at pH levels of about 5 or higher.

"Amorphous" refers to material that does not have long-range three-dimensional translational order, and is intended to include not only material which has essentially no order, but also material which may have some small degree of order, but the order is in less than three dimensions and/or is only over short distances. Partially crystalline materials and crystalline mesophases with, e.g., one- or two-dimensional translational order (liquid crystals), or orientational disorder (orientationally diosordered crystals), or with conformational disorder (conformationally disordered crystals) are intended to be included within the term "amorphous" as well.

It has been found that the aqueous concentration of the drug in a use environment tends to improve as the fraction of drug present in the amorphous state in the dispersion increases. Preferably, at least a major portion of the drug in the dispersion is amorphous. As used herein, the term "a major portion" of the drug means that at least about 60% of the drug in the dispersion is in the amorphous form, as opposed to the crystalline form; in other words, the amount of drug in crystalline form does not exceed about 40 wt %. Preferably the drug in the dispersion is "substantially amorphous," meaning that at least about 75 wt % of the drug in the dispersion is amorphous; in other words, the amount of drug in crystalline form does not exceed about 25 wt %. Even more preferably, the drug in the dispersion is "almost completely amorphous," meaning that at least about 90 wt % of the drug in the dispersion is amorphous; in other words, the amount of drug in the crystalline form does not exceed about 10 wt %. Amounts of crystalline drug may be measured by Powder X-Ray Diffraction (PXRD), by Scanning Electron Microscope (SEM) analysis, by Differential Scanning calorimetry (DSC), or by any other known quantitative measurement.

The amorphous drug can exist as a pure phase, as a solid solution of drug homogeneously distributed throughout the polymer or any combination of these states or those states that lie between them. In cases where the drug is a low-solubility drug and concentration or bioavailability enhancement is desired, the dispersion is preferably in the form of a "solid solution," meaning that amorphous drug is homogeneous distributed throughout the dispersion polymer, and that the amount of drug present in relatively pure amorphous domains within the solid dispersion is relatively small, on the order of less than 20%, and preferably less than 10% of the total amount of drug. Such solid solutions may also be termed substantially homogeneous. Solid solutions of drug and a dispersion polymer generally are more physically stable and have improved concentration-enhancing properties relative to dispersions that are not solid solutions.

When the drug and the polymer have glass transition temperatures that differ by more than about 20° C., the fraction of drug present in relatively pure amorphous drug domains or regions within the solid amorphous dispersion can be determined by measuring the glass transition temperature ($T_g$) of the dispersion. $T_g$ as used herein is the characteristic temperature at which a glassy material, upon gradual heating, undergoes a relatively rapid (i.e., in 10 to 100 seconds) physical change from a glassy state to a rubbery state. The $T_g$ of an amorphous material such as a polymer, drug, or dispersion can be measured by several techniques, including by a dynamic mechanical analyzer (DMA), a dilatometer, a dielectric analyzer, and by DSC. The exact values measured by each technique can vary somewhat, but usually fall within 10° to 30° C. of each other. When the solid amorphous dispersion exhibits a single $T_g$, the amount of drug in pure amorphous drug domains or regions in the dispersion is generally less than about 10 wt %, confirming that the dispersion is substantially homogeneous. This is in contrast to a simple physical mixture of pure amorphous drug particles and pure amorphous polymer particles, which generally display two distinct $T_g$s, one being that of the drug and the other that of the polymer. For a solid amorphous dispersion that exhibits two distinct $T_g$s, it may be concluded that at least a portion of the drug is present in relatively pure amorphous domains. With DSC, the amount of drug present in relatively pure amorphous drug domains or regions may be determined by first measuring the $T_g$ of a substantially homogeneous dispersion with a known drug loading, to be used as a calibration standard. From such calibration data, the fraction of drug in relatively pure amorphous drug domains or regions can be determined. Alternatively, the amount of drug present in relatively pure amorphous drug domains or regions may be determined by comparing the magnitude of the heat capacity (1) that correlates to the drug's $T_g$ with (2) that which correlates to the $T_g$ of a physical mixture of amorphous drug and polymer.

To obtain the maximum level of concentration and bioavailability enhancement, particularly upon storage for long times prior to use, it is preferred that the drug remain in the amorphous state. The inventors have found that this is best achieved when the $T_g$ of the solid amorphous dispersion is substantially above the storage temperature of the dispersion. In particular, it is preferable that the $T_g$ of the dispersion is at least about 40° C. and preferably at least about 60° C. Since the dispersion's $T_g$ is a function of its water content, which in turn is a function of the relative humidity (RH) to which the dispersion is exposed, these $T_g$ values refer to the $T_g$ of the dispersion containing water in an amount that is in equilibrium with the RH existing during storage. For those aspects of the invention in which the dispersion is a solid, substantially amorphous dispersion of drug in a polymer of the invention and in which the drug itself has a relatively low $T_g$ (about 70° C. or less) it is preferred that the dispersion polymer have a $T_g$ of at least about 40° C., preferably at least about 70° C. and more preferably greater than about 100° C. Since conversion of amorphous drug to the crystalline state is related to the relative values of (1) the $T_g$ of the dispersion at the storage RH and (2) the storage temperature, the dispersions of the invention tend to remain in the amorphous state longer when stored at relatively low temperatures and low relative humidities. In addition, the inclusion of water-absorbing materials such as a desiccant in the packaging of such dispersions can lead to a higher $T_g$ during storage, thereby helping to maintain the amorphous state.

Preparation of Solid Amorphous Dispersions

Solid amorphous dispersions of the invention may be made according to any known process that results in at least 60 wt % of the drug being in the amorphous state. Such processes include mechanical, thermal and solvent-based processes. Exemplary mechanical processes include milling and extrusion; thermal processes include high temperature fusion, solvent-modified fusion and melt-congealing; and solvent processes include non-solvent precipitation, spray-coating and spray-drying. See, for example, U.S. Pat. Nos. 5,456,923 and 5,939,099, which describe formation of dispersions by extrusion processes; U.S. Pat. Nos. 5,340,591 and 4,673,564, which describe forming dispersions by milling processes; and U.S. Pat. Nos. 5,707,646 and 4,894,235, which describe the formation of dispersions by melt/congeal processes, the disclosures of all of which are incorporated by reference. Preferably, the process used to form the solid amorphous dispersion results in a substantially homogeneous dispersion, as noted above.

When the drug has a relatively low melting point, typically less than about 200° C., and preferably less than about 160° C., extrusion or melt-congeal processes that provide heat and/or mechanical energy are often suitable for forming solid amorphous dispersions. For example, drug and polymer may be blended, with or without the addition of water, and the blend fed to a twin-screw extrusion device. The processing temperature may vary from about 50° C. up to about 200° C., depending on the melting point of the drug and polymer, which is a function of the DOS of the polymer and the amount of water, if any, added. Generally, the higher the melting point of the drug and polymer, the higher the processing temperature needs to be. As a general guideline, the lowest processing temperature that produces a satisfactory dispersion (almost completely amorphous and substantially homogeneous) is chosen. Processes for forming solid amorphous dispersions using such thermal methods are described in more detail in commonly assigned U.S. patent application Ser. No. 10/066,091, the disclosure of which is incorporated herein by reference.

The formation of solid amorphous dispersions by solvent processing entails dissolution of the drug and polymer in a common solvent, followed by removal of the solvent. "Common" here means that the solvent, which can be a mixture of compounds, dissolves both the drug and the polymer. Following this dissolution step, the solvent is rapidly removed by evaporation or by mixing with a non-solvent. Exemplary processes are spray-drying, spray-coating (pan-coating, fluidized bed coating, etc.), and precipitation by rapid mixing of the polymer and drug solution with $CO_2$, water, or some other non-solvent. Solvent processes are preferred because they often allow the formation of substantially homogeneous, solid amorphous dispersions.

Solvents suitable for solvent processing can be any compound in which the drug and polymer are mutually soluble. Preferably, the solvent is also volatile with a boiling point of 150° C. or less. In addition, the solvent should have relatively low toxicity and be removed from the solid amorphous dispersion to a level that is acceptable according to The international Committee on Harmonization (ICH) guidelines. Removal of solvent to this level may require a subsequent processing step such as tray-drying. Preferred solvents include water; alcohols such as methanol and ethanol; ketones such as acetone, methyl ethyl ketone and methyl iso-butyl ketone; and various other solvents such as acetonitrile, methylene chloride and tetrahydrofuran. Lower volatility solvents such as dimethyl acetamide or dimethylsulfoxide can also be used. Mixtures of solvents, such as 50% methanol and 50% acetone, can also be used, as can mixtures with water, so long as the polymer and drug are sufficiently soluble to make the spray-drying process practicable. Generally, due to the hydrophobic nature of low-solubility drugs, non-aqueous solvents are preferred, meaning that the solvent comprises less than about 30 wt % water.

A preferred method of removing the solvent is by spray-drying. The term "spray-drying" is used conventionally and broadly refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's *Chemical Engineers' Handbook*, pages 20-54 to 20-57 (Sixth Edition 1984). More details on spray-drying processes and equipment are reviewed by Marshall, "Atomization and Spray-Drying," 50 *Chem. Eng. Prog. Monogr. Series* 2 (1954), and Masters, *Spray Drying Handbook* (Fourth Edition 1985). The strong driving force for solvent evaporation is generally provided by maintaining the partial pressure of solvent in the spray-drying apparatus well below the vapor pressure of the solvent at the temperature of the drying droplets. This is accomplished by (1) maintaining the pressure in the spray-drying apparatus at a partial vacuum (e.g., 0.01 to 0.50 atm); or (2) mixing the liquid droplets with a warm drying gas; or (3) both (1) and (2). In addition, at least a portion of the heat required for evaporation of solvent may be provided by heating the spray solution.

The solvent-bearing feed, comprising the drug and the polymere, can be spray-dried under a wide variety of conditions and still yield dispersions with acceptable properties. For example, various types of nozzles can be used to atomize the spray solution; essentially any type of nozzle may be used as long as the droplets that are formed are sufficiently small that they dry sufficiently (due to evaporation of solvent) that they do not stick to or coat the spray-drying chamber wall. Although the maximum droplet size varies widely as a function of the size, shape and flow pattern within the spray-dryer, generally droplets should be less than about 500 µm in diameter when they exit the nozzle. Examples of types of nozzles that may be used to form the solid amorphous dispersions include a two-fluid nozzle, a fountain-type nozzle, a flat fan-type nozzle and a pressure nozzle. A rotary atomizer may also be used. In a preferred embodiment, a pressure nozzle is used, as disclosed in detail in commonly assigned U.S. patent application Ser. No. 10/351,568, the disclosure of which is incorporated herein by reference.

The spray solution can be delivered to the spray nozzle or nozzles at a wide range of temperatures and flow rates. Generally, the spray solution temperature can range anywhere from just above the solvent's freezing point to about 20° C. above its ambient pressure boiling point (by pressurizing the solution) and in some cases even higher. Spray solution flow rates to the spray nozzle can vary over a wide range depending on the type of nozzle, spray-dryer size and spray-dry conditions such as the inlet temperature and flow rate of the drying gas. Generally, the energy for evaporation of solvent from the spray solution in a spray-drying process comes primarily from the drying gas.

The drying gas can, in principle, be essentially any gas, but for safety reasons and to minimize undesirable oxidation of the drug or other materials in the solid amorphous dispersion, an inert gas such as nitrogen, nitrogen-enriched air or argon is utilized. The drying gas is typically introduced into the drying chamber at a temperature between about 60° and about 300° C. and preferably between about 80° and about 240° C.

The large surface-to-volume ratio of the droplets and the large driving force for evaporation of solvent leads to rapid solidification of the droplets. Solidification times should be less than about 20 seconds, preferably less than about 10 seconds, and more preferably less than 1 second. This rapid solidification is often critical to maintaining a uniform, homogeneous dispersion of drug within the particles, as opposed to separation into drug-rich and polymer-rich phases. In a preferred embodiment, the height and volume of the spray-dryer are adjusted to provide sufficient time for the droplets to dry prior to impinging on an internal surface of the spray-dryer, as described in detail in U.S. Pat. No. 6,763,607, the disclosure of which is incorporated herein by reference. As noted above, to get large enhancements in concentration and bioavailability it is preferable to obtain as homogeneous a dispersion as possible.

Following solidification, the resulting solid powder typically stays in the spray-drying chamber for about 5 to 60 seconds, causing further evaporation of solvent. The final solvent content of the solid dispersion as it exits the dryer should be low, since this reduces the mobility of the drug molecules in the dispersion, thereby improving its stability. Generally, the solvent content of the solid amorphous dispersion as it leaves the spray-drying chamber should be less than 10 wt % and preferably less than 2 wt %. Following formation, the solid amorphous dispersion can be further dried to remove residual solvent using suitable drying processes known in the art, such as tray drying, fluid bed drying, microwave drying, belt drying, rotary drying and vacuum drying.

When formed by spray-drying, the solid amorphous dispersion is usually in the form of small particles. The mean diameter of the particles may be less than 500 µm, less than 100 µm, less than 50 µm or even less than 25 µm. When formed by other methods such as by melt-congeal or extrusion, the resulting dispersion may be sieved, ground, milled, granulated, or otherwise processed to yield a plurality of small particles.

Once the solid amorphous dispersion comprising the drug and polymer has been formed, the dispersion may be incorporated into a dosage form by processing operations such as drying, granulation, and milling.

The solid amorphous dispersion may be granulated to increase particle size and improve handling of the dispersion while forming a suitable dosage form. Preferably, the average size of the granules will range from 50 to 1000 µm. Such granulation processes may be performed before or after the composition is dried, as described above. Dry or wet granulation processes can be used for this purpose. An example of a dry granulation process is roller compaction. Wet granulation processes can include so-called low shear and high shear granulation, as well as fluid bed granulation. In these processes, a granulation fluid is mixed with the composition after the dry components have been blended to aid in the formation of the granulated composition. Examples of granulation fluids include water, ethanol, isopropyl alcohol, n-propanol, the various isomers of butanol, and mixtures thereof. A polymer may be added with the granulation fluid to aid in granulating the dispersion. Examples of suitable polymers include additional polymers of the present invention, hydroxypropyl cellulose, hydroxyethyl cellulose and hydroxypropyl methylcellulose.

If a wet granulation process is used, the granulated composition is often dried prior to further processing. Examples of suitable drying processes to be used in connection with wet granulation are the same as those described above. Where the solid amorphous dispersion is made by a solvent-based process, the composition can be granulated prior to removal of residual solvent. During the drying process, both residual solvent and granulation fluid are removed from the composition.

Once the composition has been granulated, it may then be milled to achieve the desired particle size. Any known milling process may be used, including hammer milling, ball milling, fluid-energy milling, roller milling and cutting milling.

Physical Stability

Solid amorphous dispersions of a low-solubility drug and a polymer of the invention generally display excellent physical stability. As used herein, "physical stability" or "physically stable" means either (1) resistance to the tendency of the amorphous drug present in the dispersion to crystallize or (2) when the dispersion is substantially homogeneous, resistance to the tendency of the drug to separate into drug-rich domains. Thus, a dispersion that is more physically stable than another will have either (1) a slower rate of drug crystallization or (2) a slower rate of formation of drug-rich domains. Specifically, solid amorphous dispersions of the present invention have sufficient physical stability that during storage for three weeks at 25° C. and 10% RH, less than about 10 wt % of the drug in the dispersion will crystallize, preferably less than about 5 wt %.

Without wishing to be bound by any particular theory or mechanism of action, it is believed that solid amorphous dispersions generally fall into two categories with respect to physical stability: (1) those that are thermodynamically stable (in which there is little or no driving force for crystallization of the amorphous drug in the dispersion) and (2) those that are kinetically stable or metastable (in which driving force exists for crystallization of the amorphous drug but low drug mobility slows the rate of crystallization to an acceptable level).

For thermodynamically stable dispersions, the solubility of the amorphous drug in the polymer should be approximately equal to or greater than the drug loading. By "drug loading" is meant the weight fraction of drug in the solid amorphous dispersion. Drug loading can be 10 to 20% higher than the solubility and the dispersion will still be physically stable, as the driving force for crystal nucleation is quite low.

As previously noted, it has been discovered that the solubility of the amorphous form of the low-solubility/hydrophobic drug in the polymer is related to the difference between the solubility parameters of the drug and the polymer. The smaller this difference is, the greater the drug's solubility in the polymer becomes. And as the solubility of the drug in the polymer increases, the physical stability of the dispersion increases. More specifically, it has been found that the solubility of a low-solubility drug having a solubility parameter $\delta_D$ in a polymer that has a solubility parameter $\delta_P$ is generally less than about 25 wt % when $(\delta_D-\delta_P)^2$ is about 2 or greater and the melting point of the drug is about 100° C. or greater. As a result, solid amorphous dispersions made with high drug loading, i.e., greater than about 25 wt % drug wherein $(\delta_D\delta_P)^2 \geq 2.0$ generally are not thermodynamically stable. Thus, it is preferred that $(\delta_D-\delta_P)^2$ be less than about 2, more preferably less than about 1.8, and most preferably less than about 1.5. Solid amorphous dispersions that satisfy this relationship can have higher drug loadings and better thermodynamic stability than dispersions that do not.

When drug loading in the dispersion is 10 to 20% greater than the solubility of the drug in the polymer, meaning the dispersion is supersaturated in drug, the dispersion is not thermodynamically stable and a driving force exists for phase separation of the amorphous drug in the dispersion into a drug-rich phase. Such drug-rich phases may be amorphous and microscopic, on the order of less than about 1 µm in size; amorphous and relatively large, on the order of greater than about 1 µm in size; or crystalline. Following phase separation, the dispersion can consist of two phases: (1) a drug-rich phase primarily comprising drug, and (2) a second phase comprising amorphous drug dispersed in the polymer. The amorphous drug in the drug-rich phase can convert over time from the amorphous form to the lower-energy crystalline form. The physical stability of such dispersions will generally be greater for a given drug loading (1) the lower the molecular mobility of the amorphous drug is, and (2) the lower the tendency is for the amorphous drug to crystallize from the drug-rich phases.

The dispersion's $T_g$ is an indirect measure of the molecular mobility of the drug in the dispersion; the higher the $T_g$, the lower the mobility. Molecular mobility is generally lower and physical stability greater for dispersions with high $T_g$ values. Accordingly, the ratio of the dispersion's $T_g$ to storage temperature ($T_{storage}$) (in ° K) is an accurate indicator of the relative drug mobility at a given storage temperature. In order to minimize phase separation, it is desired that the mobility of the amorphous drug in the dispersion be low. This is accomplished by maintaining a ratio of $T_g/T_{storage}$ of greater than about 1. Since typical storage temperatures can range anywhere from 5° C. to 40° C. at moderate humidity (a RH of about 20 to 75%), it is preferred that the $T_g$ of the dispersion at 50% RH be at least about 30° C., more preferably at least about 40° C., and most preferably at least about 50° C.

The $T_g$ of a solid amorphous dispersion depends on several factors, including (1) the $T_g$ of the polymer, (2) the $T_g$ of the low-solubility drug, and (3) the relative amounts of polymer and drug in the dispersions. The $T_g$ for a homogeneous blend of two amorphous materials with similar densities (as is roughly the case for many drugs and the polymers of the present invention) can be estimated from the Gordon-Taylor Equation (Gordon et al., 2 *Applied Chem.* 493 (1952)) set forth below:

$$T_{g,1,2} = \frac{w_1 T_{g1} + K w_w T_{g2}}{w_1 + K w_2}$$

where $w_1$ and $w_2$ are the weight fractions of the components 1 and 2, $T_{g1}$ and $T_{g2}$ are the glass transition temperatures of components 1 and 2, respectively, $T_{g,1,2}$ is the glass transition temperature of the mixture of components 1 and 2, and K is a constant related to the free volumes of the two components. Thus, for a given low-solubility drug, the greater the $T_g$ of the polymer, the greater the weight fraction of drug that can be in the dispersion while maintaining a $T_g$ for the dispersion of greater than about 30° C.

The compositions of the present invention allow formation of solid amorphous dispersions with a high drug loading (i.e., higher drug:polymer ratio) while still retaining good physical stability. That is, compositions comprising drug and a polymer of the present invention wherein the difference in the solubility parameters of the drug and the polymer meet the criteria outlined herein typically can contain a greater proportion of drug than a solid amorphous dispersion that does not meet the criteria, while still maintaining good physical stability.

An improvement in physical stability may be determined by comparing the rates of crystallization of the drug in (1) a test composition comprising a drug and a polymer of the invention wherein the difference in the solubility parameters of the drug and the polymer meet the criteria outlined herein and in (2) a control composition consisting of a dispersion of drug and a polymer wherein the difference in the solubility parameters does not meet the criteria. The rate of drug crystallization may be measured by determining the fraction of drug in the crystalline state in the test and control compositions over time in a typical storage environment by any standard physical measurement, such as PXRD, DSC, solid state NMR or SEM analysis. Drug in a physically stable test composition will crystallize at a slower rate than the drug in the control composition. Preferably, the drug's crystallization rate in the test composition is less than 90%, and more preferably less than 80%, of the drug's crystallization rate in the control. Thus, for example, if the drug in the control composition crystallizes at a rate of 1%/week, the drug in the test composition crystallizes at a rate of less than 0.9°/0/week. Often, much more dramatic improvements in physical stability are achieved, such as less than about 10% of the drug's crystallization rate in the control, or even less than about 0.1%/week for the hypothetical given.

An improvement in physical stability may also be determined by comparing the rates of drug phase separation of the test and control compositions. By "rate of drug phase separation" is meant the rate at which the drug separates into drug-rich amorphous regions. Rates of drug phase separation from the test and control compositions may be measured using the procedures previously described. Preferably, the rate of drug phase separation in the test composition is less than 90%, and more preferably less than 80%, of the rate of drug phase separation in the control. A preferred method of measuring rates of phase separation of drug is by differential scanning calorimetry (DSC). DSC analysis of a composition that has phase-separated drug regions will display two $T_g$s: (1) one that is close to or the same as that of pure amorphous drug, corresponding to the phase-separated drug, and (2) one that is substantially different than that of the drug, corresponding to the dispersion from which the drug has phase-separated; the amount of phase-separated drug present may be determined by comparing the magnitude of the heat capacity correlating to these two $T_g$s.

A relative degree of improvement in physical stability may also be used to characterize the improvement in physical stability obtained by the compositions of the invention. "Relative degree of improvement in physical stability" Is defined as the ratio of (1) the rate of drug crystallization or phase separation in the control composition to (2) the rate of drug crystallization or phase separation in the test composition described above. For example, if the drug in the control composition crystallizes at a rate of 10 wt %/week and the drug in the test composition crystallizes at a rate of 5 wt %/week, the relative degree of improvement in physical stability would be 10 wt %÷5 wt %, or 2. Preferably, the compositions of the present invention provide a relative degree of improvement in physical stability of at least 1.25, more preferably at least 2.0, and most preferably at least 3.0.

The particular storage conditions and time of storage to evaluate physical stability may be chosen as convenient. A stability test which may be used to test whether a composition meets the stability criteria described above is storage of the test composition and the control composition for six months at 40° C. and 75% RH. An improvement of stability for the test composition may become apparent within a shorter time, such as three to five days, and shorter storage times may be used for some drugs. When comparing compositions under storage conditions which approximate ambient conditions, e.g., 25° C. and 60% RH, the storage period may need to be from several months up to two years.

The improvement in physical stability for the compositions of the present invention allows formation of solid amorphous dispersions with a higher drug loading (i.e., higher drug:polymer ratio) while still retaining good physical stability. That is, compositions comprising drug and a polymer of the invention wherein the difference in the solubility parameters of the drug and the polymer meet the criteria outlined herein typically can contain a greater proportion of drug than a solid amorphous dispersion that does not meet the criteria, while still maintaining good physical stability.

Concentration Enhancement

The compositions of the present invention are "concentration-enhancing," meaning that when the polymer having the DOS noted herein is present in the composition it improves the concentration of the drug in a use environment relative to a control composition free from the polymer. As used herein, a "use environment" can be either the in vivo environment of the GI tract, subdermal, intranasal, buccal, intrathecal, ocular, intraaural, subcutaneous spaces, vaginal tract, arterial and venous blood vessels, pulmonary tract or intramuscular tissue of an animal, such as a mammal and particularly a human, or the in vitro environment of a test solution, such as Phosphate Buffered Saline (PBS) solution or a Model Fasted Duodenal (MFD) solution. Concentration enhancement may be determined through either in vitro dissolution tests or through in vivo tests. It has been determined that enhanced drug concentration in in vitro dissolution tests in MFD solution or PBS solution is a good indicator of in vivo performance and bioavailability. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate MFD solution is the same PBS solution wherein there is also present 7.3 mM sodium taurocholic acid and 1.4 mM of 1-palmitoyl-2-oleyl-sn-glycero-3-phosphocholine. In particular, a composition of the present invention may be dissolution-tested by adding it to MFD or PBS solution and agitating to promote dissolution, or by performing a membrane permeation test as generally described in this section and described in detail in the Examples.

Preferably, when dosed to an aqueous use environment, a composition of the present invention provides a maximum drug concentration (MDC) that is at least 1.25-fold the MDC provided by a control composition, e.g., if the MDC provided by the control composition is 100 µg/mL, then a composition of the present invention provides an MDC of at least 125 µg/mL. The control composition is conventionally the undispersed drug alone such as the crystalline drug alone in its most thermodynamically stable crystalline form; in cases where a crystalline form of the drug is unknown, the control may be amorphous drug alone. The control composition may also be the drug plus a non-concentration-enhancing diluent equivalent to the weight of polymer in the test composition. More preferably, the MDC achieved with the compositions of the present invention are at least 2-fold that of the control composition, even more preferably at least 3-fold, and most preferably at least 5-fold. Rather surprisingly, the compositions may achieve extremely large enhancements in aqueous concentration. In some cases, the MDC of very hydrophobic drugs provided by the compositions of the present invention are at least 10-fold, at least 50-fold, at least 200-fold, at least 500-fold, to more than 1000-fold that of the control composition.

Alternatively, the compositions of the present invention provide in an aqueous use environment a concentration versus time Area Under the Curve (AUC), for any period of at least 90 minutes between the time of introduction into the use environment and about 270 minutes following introduction to the use environment that is at least 1 25-fold that of the control composition. More preferably, the AUC in the aqueous use environment achieved with the compositions of the present invention are at least 2-fold, more preferably at least 3-fold, and most preferably at least 5-fold that of the control composition. For some hydrophobic drugs, the compositions may provide an AUC value that is at least 10-fold, at least 25-fold, at least 100-fold, and even more than 250-fold that of the control composition.

Alternatively, the compositions of the present invention, when dosed orally to a human or other animal, provide an AUC in drug concentration in the blood plasma or serum (or relative bioavailability) that is at least 1 25-fold that observed in comparison to the control composition. Preferably, the blood AUC is at least about 2-fold, more preferably at least about 3-fold, even more preferably at least about 4-fold, still more preferably at least about 6-fold, yet more preferably at least about 10-fold, and most preferably at least about 20-fold that of the control composition. Alternatively, the compositions of the present invention, when dosed orally to a human or other animal, provide a maximum drug concentration in the blood plasma or serum ($C_{max}$) that is at least 1.25-fold that observed in comparison to the control composition. Preferably, the $C_{max}$ is at least about 2-fold, more preferably at least about 3-fold, even more preferably at least about 4-fold, still more preferably at least about 6-fold, yet more preferably at least about 10-fold, and most preferably at least about 20-fold that of the control composition. Thus, compositions that meet the in vitro or in vivo performance criteria, or both, are considered to be within the scope of the invention.

A typical in vitro test to evaluate enhanced drug concentration can be conducted by (1) administering with agitation a test composition (the dispersion of the low-solubility or hydrophobic drug and polymer of the invention) to a test medium; (2) in a separate test, adding an appropriate amount of control composition to an equivalent amount of test medium; and (3) determining whether the measured MDC and/or AUC of the test composition in the test medium is at least 1 25-fold that provided by the control composition. In conducting such a dissolution test, the amount of test composition and control composition used is that amount which, if all the drug had dissolved, would yield a drug concentration of at least 2-fold, more preferably at least 10-fold, and most preferably at least 100-fold that of the aqueous solubility or equilibrium concentration of the drug. For some test compositions of a very low-solubility drug and polymer, it may be necessary to administer an even greater amount of the test composition to determine the MDC.

MDC and/or AUC are typically determined by measuring the concentration of dissolved drug as a function of time by sampling the test medium and plotting drug concentration in the test medium against time. The MDC is taken to be the maximum value of dissolved drug measured over the duration of the test. The aqueous AUC is calculated by integrating the concentration versus time curve over any 90-minute time period between the time of introduction of the composition into the aqueous use environment (when time equals zero) and 270 minutes following introduction to the use environment (when time equals 270 minutes). Typically, when the composition reaches its MDC rapidly, in say less than about 30 minutes, the time interval used to calculate AUC is from time equals zero to time equals 90 minutes. However, if the AUC of a composition over any 90-minute time period described above meets these criteria, then the composition is considered to be within the scope of the invention.

To avoid drug particulates that would give an erroneous determination, the test solution is either filtered or centrifuged. "Dissolved drug" is typically taken as that material that either passes a 0.45 µm syringe filter or, alternatively, the material that remains in the supernatant following centrifugation. Filtration can be conducted using a 13 mm, 0.45 µm polyvinylidine difluoride syringe filter sold by Scientific Resources under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, the use of other types of microfilters may yield values somewhat higher or lower (±10-40%) than that obtained with the filter specified above, but will still allow identification of preferred dispersions. It is recognized that this definition of "dissolved drug" encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the dissolution test.

An in vitro membrane permeation test may also be used to evaluate the compositions of the present invention, described in detail below in the Examples section.

Further details of this membrane permeation test are presented in commonly assigned U.S. Patent Application Ser. No. 60/557,897, entitled "Method and Device for Evaluation of Pharmaceutical Compositions," filed Mar. 30, 2004, the disclosure of which is incorporated herein by reference.

In general terms, a typical in vitro membrane permeation test to evaluate enhanced drug concentration can be conducted by providing a drug-permeable membrane between feed and permeate reservoirs, as described in detail in the Examples, then (1) administering a sufficient quantity of test composition (that is, the composition comprising a low-solubility drug and polymer) to a feed test medium, such that if all of the drug dissolved, the theoretical concentration of drug would exceed the equilibrium concentration of the drug by a factor of at least 2; (2) separately adding an equivalent amount of control composition to an equivalent amount of feed test medium, (3) measuring the flux of drug across the membrane from the feed to the permeate reservoir; and (4) determining whether the measured maximum flux of drug provided by the test composition is at least 1 25-fold that provided by the control composition. A composition of the invention provides concentration enhancement if, when administered to an aqueous use environment, it provides a maximum flux of drug in the above test that is at least about 1.25-fold the maximum flux provided by the control composition. Preferably, the maximum flux provided by the compositions of the invention are at least about 1.5-fold, more preferably at least about 2-fold, and most preferably at least about 3-fold that provided by the control composition.

Relative bioavailability or $C_{max}$ of drugs in the compositions of the invention can be tested in vivo in animals or humans using conventional methods for making such a determination, such as a crossover study. In an exemplary in vivo crossover study, a test composition comprising a low-solubility drug and polymer of the invention is dosed to half a group of test subjects and, after an appropriate washout period (e.g., one week) the same subjects are dosed with a control composition that consists of an equivalent quantity of crystalline drug as was dosed with the test composition, but with no polymer present. The other half of the group is dosed with the control composition first, followed by the test composition. Relative bioavailability is measured as the concentration of drug in the blood (serum or plasma) versus time AUC determined for the test group divided by the AUC in the blood provided by the control composition. Preferably, this test/control ratio is determined for each subject, and then the ratios are averaged over all subjects in the study. In vivo determinations of AUC and $C_{max}$ can be made by plotting the serum or plasma concentration of drug along the ordinate (y-axis) against time along the abscissa (x-axis). To facilitate dosing, a dosing vehicle may be used to administer the dose. The dosing vehicle is preferably water, but may also contain materials for suspending the test or control composition, provided these materials do not dissolve the composition or change the aqueous solubility of the drug in vivo The determination of AUCs is a well-known procedure and is described, for example, in Welling, "Pharmacokinetics Processes and Mathematics," ACS Monograph 185 (1986).

Excipients and Dosage Forms

The inclusion of excipients other than drug and polymer in the compositions of the invention may be useful in order to formulate the composition into tablets, capsules, suspensions, powders for suspension, creams, transdermal patches, depots, and the like. The drug and polymer composition may be added to other dosage form ingredients in essentially any manner that does not substantially alter the drug's activity. When the pharmaceutical composition is in the form of a solid amorphous dispersion, the excipients may be either physically mixed with the dispersion and/or included within the dispersion.

One very useful class of excipients is surfactants. Such materials can advantageously be employed up to 5 wt % to increase the rate of dissolution by facilitating wetting, thereby increasing the MDC, and also to inhibit crystallization or precipitation of drug by interacting with the dissolved drug by mechanisms such as complexation, formation of inclusion complexes, formation of micelles or adsorbing to the surface of solid drug, crystalline or amorphous. Suitable surfactants include fatty acid and alkyl sulfonates, such as sodium lauryl sulfate; commercial surfactants such as benzalkonium chloride (HYAMINE® 1622, available from Lonza, Inc., Fairlawn, N.J.); dioctyl sodium sulfosuccinate, DOCUSATE SODIUM™ (available from Mallinckrodt Spec. Chem., St. Louis, Mo.); polyoxyethylene sorbitan fatty acid esters (TWEEN®, available from ICI Americas Inc., Wilmington, Del.; LIPOSORB® P-20 available from Lipochem Inc., Patterson N.J.; CAPMUL® POE-0 available from Abitec Corp., Janesville, Wis.); natural surfactants such as sodium taurocholic acid, 1-palmitoyl-2-oleoyl-sn-glycero-3-phosphocholine, lecithin, and other phospholipids and mono- and diglycerides; and poloxamers.

The inclusion of pH modifiers such as acids, bases, or buffers may also be beneficial. Acids such as citric acid or succinic acid retard the dissolution of the composition, while bases such as sodium acetate or amines enhance the rate of dissolution of the composition.

Other conventional formulation excipients may be employed in the compositions of the invention, including those excipients well known in the art as described for example in *Remington: The Science and Practice of Pharmacy* (20$^{th}$ Ed. 2000). Generally, excipients such as matrix materials, diluents, fillers, disintegrating agents, solubilizers, drug complexing agents, pigments, binders, lubricants, glidants, flavorants, and so forth may be used for customary purposes and in typical amounts without adversely affecting the properties of the compositions.

Examples of matrix materials, fillers, or diluents include lactose, mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers, and hydroxypropyl methyl cellulose.

Examples of drug-complexing agents or solubilizers include the polyethylene glycols, caffeine, xanthene, gentisic acid and cyclodextrins.

Examples of disintegrants include sodium starch glycolate, sodium carboxymethyl cellulose, calcium carboxymethyl cellulose, croscarmellose sodium, crospovidone (polyvinylpolypyrrolidone), methylcellulose, microcrystalline cellulose, powdered cellulose, starch, pregelatinized starch, and sodium alginate.

Examples of tablet binders include acacia, alginic acid, carbomer, carboxymethyl cellulose sodium, dextrin, ethylcellulose, gelatin, guar gum, hydrogenated vegetable oil, hydroxyethyl cellulose, hydroxypropyl cellulose, hydroxypropyl methyl cellulose, methyl cellulose, liquid glucose, maltodextrin, polymethacrylates, povidone, pregelatinized starch, sodium alginate, starch, sucrose, tragacanth, and zein.

Examples of lubricants include calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate.

Examples of Glidants Include Silicon Dioxide, Talc and Cornstarch

Compositions of the invention may also be used in a wide variety of dosage forms for administration of drugs. Exemplary dosage forms are powders or granules that may be taken orally either dry or reconstituted by addition of water or other liquids to form a paste, slurry, suspension or solution; tablets; capsules; multiparticulates; and pills. Various additives may be mixed, ground, or granulated with the compositions of this invention to form a material suitable for such dosage forms.

Compositions of the invention may be formulated in forms such that they are delivered as a suspension of particles in a liquid vehicle. Such suspensions may be formulated as a liquid or paste at the time of manufacture, or they may be formulated as a dry powder with a liquid, typically water, added at a later time but prior to oral administration. Such powders that are constituted into a suspension are often termed a sachet or an oral powder for constitution (OPC). Such dosage forms can be formulated and reconstituted by any known procedure. The simplest approach is to formulate the dosage form as a dry powder that is reconstituted by simply adding water and agitating. Alternatively, the dosage form may be formulated as a liquid and a dry powder that are combined and agitated to form the oral suspension. In yet another embodiment, the dosage form can be formulated as two powders that are reconstituted by first adding water to one powder to form a solution to which the second powder is combined with agitation to form the suspension.

Generally, it is preferred that the dispersion of drug be formulated for long-term storage in the dry state as this promotes the chemical and physical stability of the drug.

Compositions of the invention may be delivered by a wide variety of routes, including, but not limited to, oral, nasal, rectal, vaginal, subcutaneous, intravenous and pulmonary. Generally, oral delivery is preferred.

Other features and embodiments of the invention will become apparent from the following Examples that are given for illustrating the invention rather than for limiting its intended scope.

EXAMPLES

Synthesis of HPMCA$_{jk}$P Polymers

HPMCA$_{jk}$P polymers were synthesized wherein the alkanyl group was acetyl. Polymer 1, having the DOS shown in Table 1, was synthesized using the following procedure. About 160 mL of glacial acetic acid was added to a 250 mL round bottom flask equipped with a water condenser, a stir bar, an inert atmosphere purge, and placed into an oil bath at 85° C. To this, 10.02 g of HPMC (E3 Prem LV from Dow Chemical Co, having a DOS$_M$ of 1.88 and a DOS$_{HP}$ of 0.25 and 20.25 g of sodium acetate were added and allowed to dissolve. Once complete dissolution of the HPMC occurred, 15.01 g of phthalic anhydride and 41.00 g acetic anhydride were added and the mixture was allowed to react for 18 hours.

The reaction mixture was quenched into about 600 mL of water at room temperature to precipitate HPMCAP as Polymer 1, which was then filtered using a Buchner funnel. Polymer 1 was then purified by dissolving it in acetone, precipitating it in about 600 mL water, filtering it and drying it in vacuo to yield a white solid. The DOS$_{AC}$ and DOS$_S$ on the polymer were determined using the procedures previously described and the results are given in Table 1. The DOS$_M$ and DOS$_{HP}$ were assumed to be unchanged from the HPMC starting material.

The solubility parameter for Polymer 1 was calculated using the group contribution methods of Barton, previously described. The result of this calculation is given in Table 1. The T$_g$ of the polymer was also determined using Differential Scanning calorimetry (DSC) at <5% RH and is included in Table 1. Also included in Table 1 for comparison are the DOS values, $T_g$ and solubility parameter for the HPMC starting material and for a commercially available grade of hydroxypropyl methyl cellulose phthalate (HPMCP, HP-55, Shin Etsu, Tokyo, Japan).

Ten additional HPMCAP polymers (Polymers 2-11) were prepared with the DOS values, $T_g$s and solubility parameters given in Table 1, using the procedure described above, with the exceptions noted in Table 2.

to dissolve. Once complete dissolution of the HPMCT occurred, 60 mL of acetic anhydride was added and the mixture was allowed to react for 18 hours.

The reaction mixture was quenched into about 2 L of water at room temperature, precipitating the $HPMCA_{lk}T$ polymer. The polymer was rinsed with an additional liter of water, filtered using a Buchner funnel, and dried in vacuo to yield a white solid. The polymer's $DOS_{Alk}$ and $DOS_T$ were deter-

TABLE 1

| Polymer | $DOS_{HP}$ | $DOS_M$ | $DOS_{Alk}$ | $DOS_P$ | Total DOS* | $T_g$ (° C. at <5% RH) | Solubility Parameter $(J/cm^3)^{1/2}$ |
|---|---|---|---|---|---|---|---|
| HPMC | 0.25 | 1.88 | 0 | 0 | 1.88 | 142 | 25.3 |
| HPMCP | 0.26 | 1.88 | 0 | 0.68 | 2.56 | 132 | 24.9 |
| 1 | 0.25 | 1.88 | 0.61 | 0.19 | 2.65 | 98 | 23.0 |
| 2 | 0.25 | 1.88 | 0.80 | 0.16 | 2.81 | 123 | 22.3 |
| 3 | 0.25 | 1.88 | 0.90 | 0.09 | 2.84 | 121 | 21.9 |
| 4 | 0.25 | 1.88 | 0.85 | 0.10 | 2.83 | 123 | 22.0 |
| 5 | 0.25 | 1.88 | 0.83 | 0.12 | 2.83 | 123 | 22.1 |
| 6 | 0.25 | 1.88 | 0.71 | 0.15 | 2.74 | 125 | 22.5 |
| 7 | 0.25 | 1.88 | 0.64 | 0.17 | 2.69 | 106 | 22.8 |
| 8 | 0.25 | 1.88 | 0.74 | 0.18 | 2.80 | 126 | 22.5 |
| 9 | 0.25 | 1.88 | 0.63 | 0.20 | 2.71 | 128 | 22.8 |
| 10 | 0.25 | 1.88 | 0.79 | 0.13 | 2.80 | 123 | 22.2 |
| 11** | 0.21 | 1.42 | 1.23 | 0.19 | 2.84 | 132 | 23.0 |

*Total DOS = $DOS_M$ + $DOS_{Alk}$ + $DOS_P$
**Dow K3 Prem starting material

TABLE 2

| Polymer | Glacial acetic acid amount | HPMC Mass (g) | Acetic Anhydride Mass (g) | Phthalic Anhydride Mass (g) | Reaction Time (hr) |
|---|---|---|---|---|---|
| 1 | 160 mL | 10.02 | 41.00 | 15.01 | 18 |
| 2 | 100 g | 10.02 | 44.60 | 10.01 | 18.5 |
| 3 | 100 g | 10.01 | 47.40 | 6.04 | 18.5 |
| 4 | 99 g | 10.03 | 44.50 | 10.06 | 15.5 |
| 5 | 100 mL | 10.00 | 32.52 | 10.00 | 16 |
| 6 | 100 mL | 10.00 | 45.00 | 10.01 | 7.5 |
| 7 | 100 mL | 10.02 | 45.02 | 12.00 | 7.5 |
| 8 | 100 mL | 10.01 | 52.02 | 10.00 | 6.5 |
| 9 | 100 mL | 10.00 | 46.00 | 10.00 | 7 |
| 10 | 100 mL | 10.01 | 32.54 | 8.01 | 16 |
| 11 | 100 mL | 10.00 | 43.18 | 12.01 | 16 |

Synthesis of $HPMCA_AT$ Polymers $HPMCA_{lk}T$ polymers were synthesized. Polymer 12, having the DOS shown in Table 3, was synthesized using the following procedure. About 200 mL of glacial acetic acid was added to a 500 mL round bottom flask equipped with a water condenser and a stir bar and placed into an oil bath set at 85° C. To this, 20.12 g of HPMCT (from Shin Etsu, Tokyo, Japan, having a $DOS_M$ of 1.41, a $DOS_{HP}$ of 0.16, and a $DOS_T$ of 0.55), and 20.73 g of sodium acetate were added and allowed mined as noted above; the results are given in Table 3. The $DOS_M$ and $DOS_{HP}$ were assumed to be unchanged from the HPMCT starting material. The properties of the HPMCT are also given in Table 3.

The solubility parameter and $T_g$ for $HPMCA_{lk}T$ Polymer 12 were determined in the same manner as for Polymers 1-11, and are reported in Table 3.

Six additional $HPMCA_{lk}T$ polymers (Polymers 13-18) were prepared with the DOS, $T_g$ values and solubility parameters reported in Table 3, using the same procedure as for Polymers 1-11, with the following exceptions. To synthesize Polymers 13-17, HPMC (E3 Prem LV from Dow Chemical Co., having a $DOS_M$ of 1.88 and a $DOS_{HP}$ of 0 25) was first added to the glacial acetic acid and dissolved, followed by the addition of sodium acetate, trimellitic anhydride, and acetic anhydride, allowing each chemical to dissolve before adding the next. For Polymer 18 wherein the alkanyl group was propionyl, the same brand HPMC was added to glacial propionic acid and dissolved, followed by the addition of sodium propionate, trimellitic anhydride, and propionic anhydride, again allowing each chemical to dissolve before adding the next. A summary of the types and amounts of reaction materials and reaction times for $HPMCA_{lk}T$ Polymers 12-18 is given in Table 4.

TABLE 3

| Polymer | Alkanyl Group | $DOS_{HP}$ | $DOS_M$ | $DOS_{Alk}$ | $DOS_T$ | Total DOS | $T_g$ (° C. at <5% RH) | Solubility Parameter $(J/cm^3)^{1/2}$ |
|---|---|---|---|---|---|---|---|---|
| HPMCT | None | 0.16 | 1.41 | 0 | 0.55 | 1.96 | 174 | 27.4 |
| 12 | Acetyl | 0.16 | 1.41 | 0.71 | 0.23 | 2.35 | 166 | 24.8 |
| 13 | Acetyl | 0.25 | 1.88 | 0.91 | 0.18 | 2.98 | 136 | 21.8 |
| 14 | Acetyl | 0.25 | 1.88 | 1.00 | 0.09 | 2.97 | 129 | 21.3 |
| 15 | Acetyl | 0.25 | 1.88 | 0.83 | 0.09 | 2.80 | 134 | 21.9 |
| 16 | Acetyl | 0.25 | 1.88 | 0.71 | 0.18 | 2.77 | 140 | 22.5 |
| 17 | Acetyl | 0.25 | 1.88 | 1.01 | 0.10 | 2.99 | 129 | 21.3 |
| 18 | Propionyl | 0.25 | 1.88 | 0.57 | 0.28 | 2.73 | 140 | 22.9 |

TABLE 4

| Polymer | Alkyl acid (mL) | Starting Polymer Grade | Starting Polymer Mass (g) | Alkanyl Anhydride Amount | Trimellitic Anhydride Mass (g) | Reaction Time (hr) |
|---|---|---|---|---|---|---|
| 12 | 200 | HPMCT | 20.12 | 60 mL | 0 | 17 |
| 13 | 100 | Dow E3 Prem LV | 10.00 | 42.11 g | 10.14 | 16 |
| 14 | 100 | Dow E3 Prem LV | 10.01 | 42.00 g | 6.03 | 15 |
| 15 | 200 | Dow E3 Prem LV | 20.00 | 90.01 g | 10.04 | 5.25 |
| 16 | 200 | Dow E3 Prem LV | 20.00 | 90.00 | 8.02 | 5 |
| 17 | 200 | Dow E3 Prem LV | 20.01 | 90.00 | 11.01 | 16 |
| 18 | 100 | Dow E3 Prem LV | 10.00 | 57.04 | 9.05 | 7 |

Synthesis of $CA_{lk}S$ Polymers $CA_{lk}S$ polymers were synthesized. Polymer 19, having the $DOS_{Alk}$ and $DOS_s$ shown in Table 5, was synthesized using the following procedure. About 100 mL of anhydrous pyridine as a solvent and a catalyst was added to a round bottom flask equipped with an argon sparger, water condenser, and stir bar, and placed into an oil bath at 85° C. To this, 5.00 g of cellulose acetate (CA) (CA-320s, from Eastman Chemical Co. having a $DOS_{Ac}$ of 1 76) was added, and the solution was heated to reflux to dissolve the polymer. Once complete dissolution of the CA occurred, 2.68 g of succinic anhydride was added and the mixture was allowed to react for 6.5 hours.

The reaction mixture was quenched into about 700 mL of water at room temperature, and the pH was lowered to 5 with about 100 mL of 0.6N HCl to precipitate the $CA_{lk}S$ as Polymer 19 which was then filtered using a Buchner funnel and washed with about 200 mL water. Polymer 19 was then purified by dissolving it in acetone, precipitating it in 500 mL water, washing it again with 300 mL water, then drying it in vacuo to yield an off-white solid. $DOS_{Alk}$ and $DOS_S$ on $CA_{lk}S$ Polymer 19 was determined using High Performance Liquid Chromatography (HPLC); the results are given in Table 5.

The $T_g$ of Polymer 19 was determined using Differential Scanning calorimetry (DSC) at <5% relative humidity (RH) and is reported in Table 5. The solubility parameter $[(J/cm_3)^{1/2}]$ for Polymer 19 was also determined using the group contribution methods of Barton, previously described. The result of this calculation is given in Table 5. Also included in Table 5 are qualitative descriptions of solutions containing 3 mg/mL polymer, at pH 6.5 and pH 7.4.

Eight additional $CA_{lk}S$ polymers (Polymers 20-27) were prepared with the DOS and $T_g$ values given in Table 5, using the same procedure described above, with the exceptions noted in Table 6. The solubility parameters were also calculated as noted above, and are given in Table 5.

For Polymers 21 and 25, the $DOS_{AC}$ was increased prior to addition of succinate groups as follows. A 15.00 g sample of CA-320s was added to about 300 mL of anhydrous pyridine in a round bottom flask equipped with an argon sparger, water condenser, and stir bar, and placed into an oil bath set at 85° C. Next, 2.52 g of acetic anhydride was added and the mixture was allowed to react for 5 hours. The reaction mixture was quenched into about 1800 mL of room temperature water to precipitate the polymer. The polymer was then filtered and dissolved in 500 mL acetone, precipitated in 1600 mL water, filtered and rinsed with water, and dried in vacuo. $CA_{lk}S$ was then formed using this acetylated CA-320s starting material by the procedure described above, with the exceptions noted in Table 6.

For Polymers 22 and 23, 20.02 g CA-320s were added to 200 mL glacial acetic acid in an oil bath set at 85° C. and stirred for about 5 hours until the polymer was completely dissolved. Next, 20.04 g sodium acetate and 6.02 g succinic anhydride were added and the mixture was allowed to react for about 12 hours. Polymer 22 was precipitated, filtered, and dried using the procedure described above.

TABLE 5

| Polymer* | $DOS_{Alk}$ | $DOS_S$ | Total DOS | $DOS_{Alk}/DOS_S$ | $T_g$ (° C. at <5% RH) | Solubility Parameter $(J/cm^3)^{1/2}$ | Solubility (3 mg/mL) pH 6.5 | Solubility (3 mg/mL) pH 7.4 |
|---|---|---|---|---|---|---|---|---|
| 19 | 1.69 | 0.76 | 2.46 | 2.2 | ND* | 26.04 | ND | ND |
| 20 | 1.69 | 0.59 | 2.28 | 2.9 | 176.28 | 26.42 | clear | ND |
| 21 | 1.88 | 0.40 | 2.28 | 4.7 | ND | 26.13 | hazy | clear |
| 22 | 1.75 | 0.25 | 2.0 | 7.0 | 190.71 | 27.07 | hazy | hazy |
| 23 | 1.84 | 0.38 | 2.22 | 4.8 | 187.04 | 26.34 | hazy | clear |
| 24 | 1.64 | 1.06 | 2.71 | 1.5 | 158.09 | 25.61 | clear | ND |
| 25 | 2.28 | 0.54 | 2.82 | 4.2 | ND | 24.40 | insoluble | clear |
| 26 | 2.11 | 0.82 | 2.93 | 2.6 | 166.40 | 24.51 | ND | ND |
| 27 | 1.65 | 0.5 | 2.15 | 3.3 | ND | 26.81 | clear | clear |

*The alkanyl group was acetate for all polymers
**ND = not determined

TABLE 6

| Polymer | Method of Preparation | Starting Amount of solvent (ml) | Starting Polymer Type | Starting Polymer Mass (g) | Succinic Anhydride Mass (g) | Reaction Time (hr) |
|---|---|---|---|---|---|---|
| 19 | pyridine | 100 | CA-320s | 5.00 | 2.68 | 6.5 |
| 20 | pyridine | 100 | CA-320s | 10.01 | 5.37 | 16 |
| 21 | pyridine | 200 | Acetylated CA-320s | 11.08 | 6.51 | 5 |
| 22 | acetic acid Na acetate | 200 20.04 g | CA-320s | 20.02 | 6.02 | 12 |
| 23 | acetic acid Na acetate | 200 20.19 g | CA-320s | 20.03 | 8.29 | 12 |
| 24 | pyridine | 160 | CA-320s | 7.61 | 12.50 | 5 |
| 25 | pyridine | 85 | Acetylated CA-320s | 3.02 | 8.04 | 20 |

TABLE 6-continued

| Polymer | Method of Preparation | Amount of solvent (ml) | Starting Polymer Type | Mass (g) | Succinic Anhydride Mass (g) | Reaction Time (hr) |
|---|---|---|---|---|---|---|
| 26 | pyridine | 50 | CA-320s | 2.51 | 1.34 | 4.5 |
| 27 | pyridine | 100 | CA-320s | 5.03 | 2.68 | 6 |

Synthesis of $MCA_{Ik}S$ Polymers $MCA_{Ik}S$ polymers were synthesized as follows. Polymer 28 having the $DOS_M$ shown in Table 7 was synthesized using the following procedure. A 10.00 g sample of methyl cellulose (Metalose SM-4 from Shin Etsu), having a $DOS_M$ of 1.75 was added to 200 mL glacial acetic acid in an oil bath at 85° C. and stirred for about 5 hours until the polymer was completely dissolved. Next, 20.05 g sodium acetate, 32.01 g acetic anhydride, and 6.01 g succinic anhydride were added and the mixture was allowed to react for about 12 hours. The reaction mixture was then quenched and the resulting $MCA_{Ik}S$ polymer was purified using the procedures described above for the $CA_{Ik}S$ polymers. Details of the reaction conditions are given in Table 8.

Two additional $MCA_{Ik}S$ polymers (Polymers 29 and 30) were prepared with the DOS given in Table 7, using the same procedure described above, with the exceptions noted in Table 8. The solubility parameters were also calculated as noted above, and are given in Table 7.

TABLE 7

| Polymer* | $DOS_M$ | $DOS_{Alk}$ | $DOS_S$ | Total DOS | $DOS_{M+Alk}$ | $DOS_{M+Alk}/DOS_S$ | $T_g$ (° C. at <5% RH) | Solubility Parameter $(J/cm^3)^{1/2}$ |
|---|---|---|---|---|---|---|---|---|
| 28 | 1.75 | ND | ND | ND | ND | ND | 151 | ND |
| 29 | 1.75 | 0.89 | 0.17 | 2.81 | 2.64 | 15.5 | ND | 22.2 |
| 30 | 1.75 | 0.51 | 0.47 | 2.73 | 2.26 | 4.8 | ND | 23.2 |

*The alkanyl group was acetate for all polymers.
*ND = not determined

TABLE 8

| Polymer | Starting Polymer Mass (g) | Solvent (mL) | Sodium Acetate Mass (g) | Succinic Anhydride Mass (g) | Acetic Anhydride Mass (g) | Reaction Time (hr) |
|---|---|---|---|---|---|---|
| 28 | 10.00 | Acetic acid (200) | 20.05 | 6.01 | 32.01 | 12 |
| 29 | 5.01 | Pyridine (100) | — | 0.63 | 25 | 7 |
| 30 | 10.03 | Acetic acid (200) | 20.20 | 18.00 | 57.77 | 9 |

Drugs Used in Examples

The following drugs were used in the Examples described below.

Drug 1 was torcetrapib having the structure previously noted, an aqueous solubility of less than 0.1 μg/mL, and a Log P value of 7.0, as determined by the average value estimated using Crippen's, Viswanadhan's, and Broto's fragmentation methods. The $T_g$ of amorphous Drug 1 was determined by DSC analysis to be 29° C. and its solubility parameter was calculated to be 20 86 $(J/cm^3)^{1/2}$.

Drug 2 was 2-(2-chloro-4-iodophenylamino)-N-cyclopropylmethoxy-3,4-difluorobenzamide, having the structure:

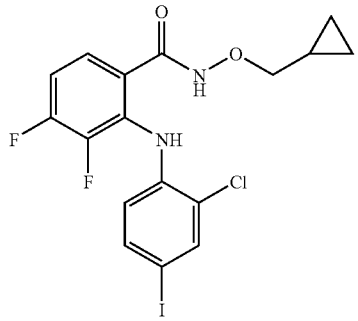 [SMILES: O=C(NOCC1CC1)c1ccc(F)c(F)c1Nc1ccc(I)cc1Cl]

Drug 2 had an aqueous solubility of less than 0.1 μg/mL, and a Log P value of 5.8, as determined by the average value estimated using Crippen's, Viswanadhan's, and Broto's fragmentation methods. The $T_g$ of amorphous Drug 2 was determined by DSC analysis to be 46° C. and its solubility parameter was calculated to be 27.25 $(J/cm^3)^{1/2}$.

Drug 3 was 2-[4-(4-chlorobenzoyl)phenoxy]-2-methylpropanoic acid 1-methylethyl ester, also known as fenofibrate, having the structure:

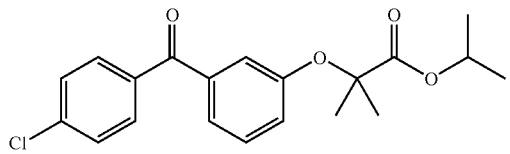 [SMILES: CC(C)OC(=O)C(C)(C)Oc1cccc(C(=O)c2ccc(Cl)cc2)c1]

Drug 3 had an aqueous solubility of about 0.1 μg/mL, and a Log P value of 4.8, as determined by the average value estimated using Crippen's, Viswanadhan's, and Broto's fragmentation methods. The $T_g$ of amorphous Drug 3 was determined to be about −20° C., while the melting point for the crystalline drug was 79-82° C. The solubility parameter of Drug 3 was determined to be about 22.7 $(J/cm^3)^{1/2}$.

Drug 4 was 5-(2-(4-(3-benzisothiazolyl)-piperazinyl) ethyl-6-chlorooxindole, also known as ziprasidone, having the structure:

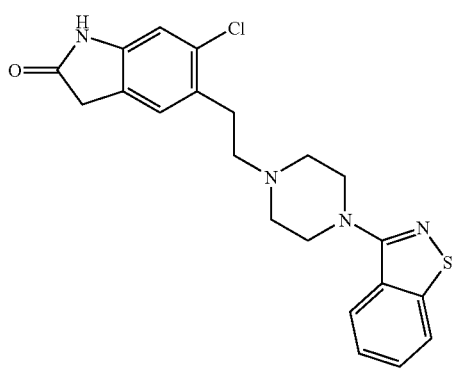 [SMILES: O=C1Cc2cc(CCN3CCN(c4nsc5ccccc45)CC3)c(Cl)cc2N1]

The free base form of Drug 4 had an aqueous solubility of less than 0.1 μg/mL, while the aqueous solubility of the hydrochloride salt form was about 10 μg/mL. Drug 4 had a Log P value of 4.7, as determined by the average value estimated using Crippen's, Viswanadhan's, and Broto's fragmentation methods. In the Examples below, Drug 4 was in the hydrochloride or tosylate salt form. The $T_g$ of amorphous Drug 4 (free base) was determined by DSC analysis to be about 72° C., and the melting point of the free base was about 224° C. The solubility parameter of Drug 4 was calculated to be 29.29 $(J/cm^3)^{1/2}$.

Example 1

For Example 1, a solid amorphous dispersion (Dispersion 1) of 50 wt % Drug 1 and 50 wt % Polymer 1 was prepared using a spray-drying process as follows. A spray solution was prepared by dissolving 521.2 mg Drug 1 and 520.1 mg Polymer 1 in 20 mL of methanol. This solution was spray-dried using a custom-made spray-dryer, which consisted of an atomizer in the top cap of a vertically oriented 11-cm diameter stainless steel pipe. The atomizer was a two-fluid nozzle (Spraying Systems Co. 1650 fluid cap and 64 air cap), and the atomizing gas was nitrogen delivered to the nozzle at 80° C. and at a flow rate of 15 g/min. The solution to be spray-dried was delivered to the nozzle at room temperature and at a flow rate of 1.3 mL/min using a syringe pump. Filter paper with a supporting screen was clamped to the bottom end of the pipe to collect the solid spray-dried material and allow the nitrogen and evaporated solvent to escape. The spray-drying parameters are summarized in Table 9.

Examples 2-12

For Examples 2-12, spray-dried Dispersions 2-12 were prepared as in Example 1 except that the drug type, drug loading and polymer were varied as noted in Table 9.

Examples 13-14

Physical Mixtures 1-2 of Drug 5 and the polymers of the present invention were prepared using the following procedure. Drug and polymer were weighed into scintillation vials, mixed for 20 minutes using a Turbula mixer, sieved through a 20-mesh screen, then mixed again for 20 minutes. The ingredients and amounts are summarized in Table 10.

TABLE 10

| Example No. | Physical Mixture | Drug | Drug Mass (mg) | Polymer | Polymer Mass (mg) | Drug Loading (wt % A) |
|---|---|---|---|---|---|---|
| 13 | 1 | 5 HCl salt | 392.4 | 2 | 608.1 | 36 |
| 14 | 2 | 5 tosylate salt | 511.0 | 6 | 490.5 | 36 |

In Vitro Evaluation of Concentration Enhancement of Dispersions 1-10

Dispersions 1-10 were evaluated in a microcentrifuge dissolution test using the following procedure. For this test, each dispersion was added to a microcentrifuge tube in an amount such that the concentration of Drug 1 would have been 1000 mgA/mL, had all of the drug dissolved. Control C1 consisted of crystalline Drug 1 alone, and was tested for comparison. The tubes were placed In a 37° C. temperature-controlled chamber, and 1.8 mL phosphate buffered saline (PBS) at pH 6.5 and 290 mOsm/kg was added to each tube. The samples were mixed in a vortex mixer for about a minute. The samples were then centrifuged at 13,000 G at 37° C. for one minute. The resulting supernatant solutions were then sampled and diluted 1:6 (by volume) with methanol and then analyzed by HPLC. The contents of the tubes were mixed on the vortex mixer and allowed to stand undisturbed at 37° C. until the next sample was taken. Samples were collected at 4, 10, 20, 40, 90, and 1200 minutes.

The concentrations of Drug 1 obtained in these samples were used to determine the values of the maximum drug concentration between 0 and 90 minutes ($MDC_{90}$) and the area under the curve from 0 to 90 minutes ($AUC_{90}$). The results are shown in Table 11.

TABLE 9

| Example | Dispersion | Drug | Drug Mass (mg) | Polymer | Polymer Mass (mg) | Solvent | Solvent amount | Drug Loading (wt % A)* |
|---|---|---|---|---|---|---|---|---|
| 1 | 1 | 1 | 521.2 | 1 HPMCAP | 520.1 | Methanol | 20 mL | 50 |
| 2 | 2 | 1 | 130.2 | 1 HPMCAP | 399.8 | Acetone | 14 g | 25 |
| 3 | 3 | 1 | 250.9 | 2 HPMCAP | 250.9 | Acetone | 20 mL | 50 |
| 4 | 4 | 1 | 102.5 | 2 HPMCAP | 307.6 | Acetone | 20 mL | 25 |
| 5 | 5 | 1 | 250.9 | 9 HPMCAP | 750.3 | Acetone | 28 g | 25 |
| 6 | 6 | 1 | 250.4 | 8 HPMCAP | 749.9 | Acetone | 28 g | 25 |
| 7 | 7 | 1 | 250.0 | 6 HPMCAP | 750.0 | Acetone | 28 g | 25 |
| 8 | 8 | 1 | 250.2 | 14 HPMCAT | 749.9 | Acetone | 30 g | 25 |
| 9 | 9 | 1 | 250.6 | 15 HPMCAT | 749.7 | Acetone | 28 g | 25 |
| 10 | 10 | 1 | 250.0 | 13 HPMCAT | 750.0 | Acetone | 28 g | 25 |
| 11 | 11 | 2 | 100 | 5 HPMCAP | 300 | Acetone | 14 g | 25 |
| 12 | 12 | 3 | 150.2 | 10 HPMCAP | 450.1 | Acetone | 20 g | 25 |

*wt % A = wt % of active form of drug

TABLE 11

| Sample | Drug 1 loading (wt % A) | Polymer | MDC$_{90}$ (μgA/mL) | AUC$_{90}$ (min · μgA/mL) |
|---|---|---|---|---|
| Dispersion 1 | 50 | 1 HPMCAP | 99 | 8,000 |
| Dispersion 2 | 25 | 1 HPMCAP | 575 | 43,500 |
| Dispersion 3 | 50 | 2 HPMCAP | 175 | 2,000 |
| Dispersion 4 | 25 | 2 HPMCAP | 86 | 1,300 |
| Dispersion 5 | 25 | 9 HPMCAP | 28 | 1,900 |
| Dispersion 6 | 25 | 8 HPMCAP | 714 | 59,100 |
| Dispersion 7 | 25 | 6 HPMCAP | 743 | 58,000 |
| Dispersion 8 | 25 | 14 HPMCAT | 840 | 45,800 |
| Dispersion 9 | 25 | 15 HPMCAT | 48 | 2,800 |
| Dispersion 10 | 25 | 13 HPMCAT | 915 | 70,500 |
| Control C1 | 100 | — | <1 | <88 |

As can be seen from the data, Dispersions 1-10 provided concentration enhancement of Drug 1 relative to Control C1. The MDC$_{90}$ values provided by Dispersions 1-10 were from at least 28- to at least 915-fold that of Control C1, while the AUC$_{90}$ values were from at least 15- to at least 801-fold that of Control C1.

In Vitro Evaluation of Dispersion 3

Dispersion 3 was evaluated in vitro in comparison to Control C1 using the membrane permeation test described below.

An Accurel® PP 1E microporous polypropylene membrane was obtained from Membrana GmbH (Wuppertal, Germany). The membrane was washed in isopropyl alcohol and rinsed in methanol in a sonicating bath for one minute at ambient temperature, and then allowed to air dry at ambient temperature. The feed side of the membrane was then plasma-treated to render it hydrophilic by placing a sample of the membrane in a plasma chamber. The atmosphere of the plasma chamber was saturated with water vapor at a pressure of 550 mtorr. A plasma was then generated using radio frequency (RF) power inductively coupled into the chamber via annular electrodes at a power setting of 50 Watts for 45 seconds. The contact angle of a drop of water placed on the surface of the plasma-treated membrane was about 40°. The contact angle of a drop of water placed on the permeate side of the same membrane was greater than about 110°.

A permeate reservoir was formed by capping the open end of a glass tube having an inside diameter of about 2 54 cm by gluing a sample of the plasma-treated membrane to the tube using an epoxy-based glue (LOCTITE® E-30CL HYSOL® from Henkel Loctite Corp, Rocky HUI, Conn.). The membrane was oriented so that its feed side was on the outside of the permeate reservoir and its permeate side was on the inside of the reservoir. The effective membrane area of the membrane capping the permeate reservoir was about 4.9 cm$^2$. The permeate reservoir was placed into a glass feed reservoir. The feed reservoir was equipped with a magnetic stir bar and the reservoir was placed on a stir plate and the stir rate was set to 100 rpm during the test. The apparatus was placed into a chamber maintained at 37° C. for the duration of the test.

To form the feed solution, a 1.2 mg sample of Dispersion 3 was weighed into the feed reservoir. To this was added 5 mL of an aqueous solution designed to model the fed state, consisting of a Phosphate Buffered Solution (PBS) containing 29.2 mM or 2 wt % sodium taurocholic acid and 5.6 mM of 1-palmitoyl-2-oleyl-sn-glycero-3-phosphocholine (NaTC/POPC). Had all the drug dissolved, the concentration of Drug 1 in the feed solution would have been 120 μg/mL. The feed solution was mixed using a vortex mixer for 1 minute. Before the membrane contacted the feed solution, 5 mL of 20 wt % decanol in decane was placed into the permeate reservoir. Time zero in the test was when the membrane was placed in contact with the feed solution. A 50 μL aliquot of the permeate solution was collected at 20, 40, 60, 90, 120, 180, 240, and 350 minutes. Samples were then diluted in 250 μL isopropyl alcohol and analyzed using HPLC. In a separate test, 0.6 mg of Control C1 was added to PBS, so that, had all of the drug dissolved, the concentration of drug would have been 120 μgA/mL.

The maximum flux of drug across the membrane (in units of μgA/cm$^2$-min) was determined by performing a least-squares fit to the data to obtain the maximum slope, multiplying the slope by the permeate volume (5 mL), and dividing by the membrane area (4.9 cm$^2$). The results of this calculation are summarized in Table 12, and show that Dispersion 3 provided a maximum flux of Drug 1 through the membrane that was 2.8-fold that provided by crystalline drug, indicating that the dispersion made using Polymer 1 provided concentration enhancement of Drug 1 in the aqueous feed solution.

TABLE 12

| Sample | Drug 1 loading (wt % A) | Polymer | Feed Solution | Maximum Flux of Drug 1 (μgA/cm$^2$-min) |
|---|---|---|---|---|
| Dispersion 3 | 50 | 2 HPMCAP | 2.0 wt % NaTC/POPC | 0.258 |
| C1 | 100 | — | 2.0 wt % NaTC/POPC | 0.091 |

In Vitro Evaluation of Dispersion 11

Dispersion 11 (25:75 Drug 2:Polymer 5) was evaluated in vitro using the membrane permeation test described above, with feed solutions modeling both fasted and fed states (0.5 wt % and 2.0 wt % NaTC/POPC). Had all of the drug dissolved, the concentration of Drug 2 in the feed solution would have been 100 μgA/mL. Control C2 consisted of crystalline Drug 2 alone, tested in both 0.5 wt % and 2.0 wt % NaTC/POPC. Had all of the drug dissolved, the concentration of Control C2 drug added would have been 100 μgA/mL Drug 2.

The maximum flux of drug across the membrane (in units of μgA/cm$^2$-min) was determined by estimating the tangent to the concentration versus time curve at time 0. The results are summarized in Table 13, and show that Dispersion 11 comprising Drug 2 and the HPMCA$_{tk}$P polymer of the present invention provided concentration enhancement, providing a maximum flux of Drug 2 that was 37.3-fold that of Control C2 from 0.5 wt % NaTC/POPC, and 12 0-fold that of Control C2 from 2.0 wt % NaTC/POPC.

TABLE 13

| Sample | Drug 2 (wt % A) | Polymer | Feed Solution | Maximum Drug Flux (μgA/cm$^2$-min) |
|---|---|---|---|---|
| Dispersion 11 | 25 | 5 | 0.5% NaTC/POPC | 1.12 |
| Dispersion 11 | 25 | 5 | 2.0% NaTC/POPC | 1.20 |
| Control C2 | 100 | — | 0.5% NaTC/POPC | 0.03 |
| Control C2 | 100 | — | 2.0% NaTC/POPC | 0.10 |

In Vitro Evaluation of Dispersion 12

Dispersion 12 (25:75 Drug 3:Polymer 10) was evaluated in vitro using the membrane permeation test described above, with feed solutions modeling both fasted and fed states (0.5 wt % and 2.0 wt % NaTC/POPC). Had all of the drug dissolved, the concentration of Drug 3 in the feed solution would have been 100 µgA/mL. Control C3 consisted of crystalline Drug 3 alone, tested in both 0.5 wt % and 2.0 wt % NaTC/POPC. Had all of the drug dissolved, the concentration of Control C3 drug added would have been 100 µgA/mL.

The maximum flux of drug across the membrane (in units of µgA/cm$^2$-min) was determined by estimating the tangent to the concentration versus time curve at time 0. The results are summarized in Table 14, and show that Dispersion 12 comprising Drug 3 and the HPMCA$_{lk}$P polymer of the invention provided concentration enhancement, providing a maximum flux of Drug 3 that was 2.8-fold that of Control C3 from 0.5 wt % NaTC/POPC, and 2.0-fold that of Control C3 from 2.0 wt % NaTC/POPC.

TABLE 14

| Sample | Drug 3 (wt % A) | Polymer | Feed Solution | Maximum Drug Flux (µgA/cm$^2$-min) |
|---|---|---|---|---|
| Dispersion 12 | 25 | 10 | 0.5% NaTC/POPC | 0.97 |
| Dispersion 12 | 25 | 10 | 2.0% NaTC/POPC | 1.08 |
| Control C3 | 100 | — | 0.5% NaTC/POPC | 0.35 |
| Control C3 | 100 | — | 2.0% NaTC/POPC | 0.53 |

In Vitro Evaluation of Physical Mixtures 1 & 2

Physical Mixtures 1 and 2, consisting of Drug 4 and the polymers of the present invention, were evaluated in vitro using the membrane permeation test described above, except that the permeate solution consisted of 60 wt % decanol in decane, and the feed solution was designed to model the fasted state, consisting of PBS containing 7.3 mM sodium taurocholic acid and 1 4 mM or 0.5 wt % NaTC/POPC. Had all of the drug dissolved, the concentration of Drug 5 in the feed solution would have been 100 µgA/mL.

Controls C5 and C6 consisted of crystalline Drug 4 in the hydrochloride (C5) and tosylate (C6) salt forms, and a sufficient amount of sample was added to PBS containing 0 5 wt % NaTC/POPC, so that the concentration of drug would have been 100 µgA/mL, had if all of the drug dissolved. For Control C5, the amount of crystalline Drug 4 hydrochloride salt added to 5 mL was 0.54 mg, and for Control C6, the amount of crystalline Drug 5 tosylate salt added to 5 mL was 0.71 mg.

The maximum flux of drug across the membrane was calculated using the method described above, and the results are presented in Table 15. These data show that the Physical Mixtures of Drug 4 and the polymers of the present invention provided concentration enhancement for Drug 4 in the feed solution relative to the crystalline controls. Both Physical Mixtures 1 and 2 provided maximum fluxes that were 1.4-fold that of the crystalline control of the same salt form.

TABLE 15

| Sample | Drug 5 salt form | Drug 5 (wt % A) | Polymer | Feed Solution | Maximum Flux of Drug 5 (µgA/cm$^2$-min) |
|---|---|---|---|---|---|
| Physical Mixture 1 | HCl | 36 | 2 | 0.5 wt % NaTC/POPC | 0.138 |
| Control C5 | HCl | 100 | — | 0.5 wt % NaTC/POPC | 0.099 |
| Physical Mixture 2 | tosylate | 36 | 6 | 0.5 wt % NaTC/POPC | 0.10 |
| Control C6 | tosylate | 100 | — | 0.5 wt % NaTC/POPC | 0.07 |

Example 15

For Example 15, a solid amorphous dispersion (Dispersion 13) of 25 wt % Drug 1 and 75 wt % Polymer 19 was prepared using a spray-drying process as follows. A spray solution was prepared by dissolving 125 mg Drug 1 and 375 mg Polymer 19 in 25 g of acetone. This solution was spray-dried using a custom-made bench top spray-dryer, which consisted of an atomizer in the top cap of a vertically oriented 11-cm diameter stainless steel pipe. The atomizer was a two-fluid nozzle (Spraying Systems Co. Model 1650 fluid cap and 64 air cap), where the atomizing gas was nitrogen delivered to the nozzle at 70° C. and a flow rate of 1 SCFM, and the solution to be spray-dried was delivered to the nozzle at room temperature and at a flow rate of 1.3 mL/min using a syringe pump. Filter paper with a supporting screen was clamped to the bottom end of the pipe to collect the solid spray-dried material and allow the nitrogen and evaporated solvent to escape.

Examples 16-23

For Examples 16-23, Dispersions 14-21 of Drug 1 and CA$_{lk}$S were prepared as in Example 15 except that the drug loading and polymer were varied as noted in Table 16.

Examples 24-27

For Examples 24-27, Dispersions 22-25 of Drug 2 and CA$_{lk}$S were prepared as in Example 15 except that the drug loading and polymer were varied as noted in Table 16, and for Dispersions 24-25, the nitrogen was delivered to the nozzle at 85° C.

Example 28

For Example 28, Dispersion 26 containing Drug 4 and CA$_{lk}$S was prepared as in Example 15 except that the drug loading and polymer were varied as noted in Table 16.

Example 29

For Example 29, Dispersion 27 containing Drug 1 and MCA$_{lk}$S was prepared as in Example 15 except that drug loading and polymer were varied as noted in Table 16.

The type and amount of solvents used in the spray-drying process used for Dispersions 14-27 are also reported in Table 16.

TABLE 16

| Dispersion | Drug | Drug Mass (mg) | Polymer | Polymer Mass (mg) | Drug Loading (wt %) | Solvent | Solvent amount (g) |
|---|---|---|---|---|---|---|---|
| 13 | Drug 1 | 125 | 1 | 375 | 25 | Acetone | 25 |
| 14 | Drug 1 | 200 | 1 | 300 | 40 | Acetone | 25 |
| 15 | Drug 1 | 200 | 1 | 600 | 25 | Acetone | 26 |
| 16 | Drug 1 | 320 | 1 | 480 | 40 | Acetone | 26 |
| 17 | Drug 1 | 457.5 | 1 | 457.5 | 50 | Acetone | 28 |
| 18 | Drug 1 | 499.6 | 3 | 499.6 | 50 | Acetone | 28 |
| 19 | Drug 1 | 553.2 | 4 | 553.2 | 50 | Acetone | 28 |
| 20 | Drug 1 | 88.1 | 5 | 1671.1 | 5 | Acetone | 28 |
| 21 | Drug 1 | 24.3 | 2 | 456.6 | 5 | Acetone | 28.3 |
| 22 | Drug 2 | 161 | 8 | 107.3 | 60 | Acetone | 12 |
| 23 | Drug 2 | 151.2 | 8 | 226.8 | 40 | Acetone | 12 |
| 24 | Drug 2 | 58.8 | 5 | 1620.5 | 3.5 | Acetone | 27.7 |
| 25 | Drug 2 | 26.7 | 2 | 506.4 | 5 | Acetone | 28.2 |
| 26 | Drug 4 | 50.4 | 2 | 950.7 | 5 | 8:2 Methanol:H$_2$O | 31.2 |
| 27 | Drug 1 | 250.1 | 10 | 750.1 | 25 | Acetone | 31.5 |

In Vitro Evaluation of Concentration Enhancement

The drug concentrations provided by several of the Dispersions in the foregoing Examples were evaluated in vitro in comparison to controls comprising crystalline drug using the membrane permeation test previously described.

To form the feed solutions, 2.4 mg and 1.5 mg of Dispersions 13 and 14, respectively, were weighed into the feed reservoir. To this was added 5 mL of the Model Fasted Duodenum (MFD) solution consisting of Phosphate Buffered Saline (PBS) solution containing 7.3 mM sodium taurocholic acid and 1.4 mM of 1-palmitoyl-2-oleyl-sn-glycero-3-phosphocholine (0.5% NaTC/POPC). Had all of the drug dissolved, the concentration of Drug 1 in the feed solution would have been 120 μgA/mL. The feed solutions were each mixed using a vortex mixer for 1 minute. Before the membrane contacted the feed solutions, 5 mL of 20 wt % decanol in n-decane was placed into the permeate reservoir. Time zero in the test was when the membrane was placed in contact with the feed solution. A 504 aliquot of the permeate solution was collected at 20, 40, 60, 90, 120, 180, 240, and 350 minutes. Samples were then diluted in 250 μL isopropyl alcohol and analyzed using HPLC. Control C1 consisted of crystalline Drug 1 alone, and 0.6 mg was added so that the concentration of drug would have been 120 μgA/mL had all of the drug dissolved.

The maximum flux of drug across the membrane (in units of μgA/cm$^2$-min) was determined by performing a least-squares fit to the data to obtain the slope, multiplying the slope by the permeate volume (5 mL), and dividing by the membrane area (4.9 cm$^2$). The results of this calculation are summarized in Table 17, and show that Dispersion 13 provided a maximum flux of Drug 1 through the membrane that was 4.2-fold that provided by Control C1, and Dispersion 14 provided a maximum flux of Drug 1 through the membrane that was 5.7-fold that provided by Control C1, indicating that dispersions made using Polymer 19 provided concentration enhancement of Drug 1 in the aqueous feed solution.

TABLE 17

| Dispersion | Formulation | Feed Solution | Maximum Flux of Drug 1 (μgA/cm$^2$-min) |
|---|---|---|---|
| 13 | 25:75 Drug 1:Polymer 19 | 0.5% NaTC/POPC | 0.32 |
| 14 | 40:60 Drug 1:Polymer 19 | 0.5% NaTC/POPC | 0.43 |
| C1 | Crystalline Drug 1 | 0.5% NaTC/POPC | 0.08 |

Dispersions 13 and 14 were also evaluated in a microcentrifuge dissolution test previously described. For this test, 7.2 mg of Dispersion 13, 4.5 mg of Dispersion 14, or 1.8 mg of Control C1 were added to respective microcentrifuge tubes. The tubes were placed in a 37° C. temperature-controlled bath, and 1.8 mL PBS solution at pH 6.5 and 290 mOsm/kg were added to each tube. Had all of the drug dissolved, the concentration of Drug 1 would have been 1000 μgA/mL. The samples were mixed using a vortex mixer for about 1 minute, then centrifuged at 13,000 G at 37° C. for 1 minute. The resulting supernatant solutions were then sampled and diluted 1:6 (by volume) with methanol and then analyzed by HPLC. The contents of the tubes were mixed on the vortex mixer and allowed to stand undisturbed at 37° C. until the next sample was taken. Samples were collected at 4, 10, 20, 40, 90, and 1200 minutes.

The concentrations of Drug 1 obtained in these samples were used to determine the values of the maximum drug concentration between 0 and 90 minutes (MDC$_{90}$) and the area under the curve from 0 to 90 minutes (AUC$_{90}$). The results are shown in Table 18.

TABLE 18

| Sample | MDC$_{90}$ (μgA/mL) | AUC$_{90}$ (min · μgA/mL) |
|---|---|---|
| Dispersion 13 | 447 | 25,800 |
| Dispersion 14 | 266 | 18,500 |
| Control C1 | <1 | <100 |

As can be seen from the data, Dispersions 13 and 14 provided concentration enhancement of Drug 1 relative to Control C1. The MDC$_{90}$ provided by Dispersion 13 was greater than 447-fold that of Control C1, while the AUC$_{90}$ was greater than 258-fold that of Control C1. The MDC$_{90}$ provided by Dispersion 14 was greater than 266-fold that of Control C1, while the AUC$_{90}$ was greater than 185-fold that of Control C1.

Dispersions 22 and 23 (60:40 Drug 2:Polymer 26 and 40:60 Drug 2:Polymer 28) were evaluated in vitro using the microcentrifuge dissolution test described above, except that 1 8 mL of the MFD solution previously described was added to each tube.

Control C2 consisted of crystalline Drug 2 alone; had all of the drug dissolved, the concentration of Drug 2 added would have been 1000 μgA/mL.

The concentrations of Drug 2 obtained in these samples were used to determine the MDC$_{90}$ and AUC$_{90}$ values. The results are shown in Table 19.

TABLE 19

| Sample | $MDC_{90}$ (μgA/mL) | $AUC_{90}$ (min · μgA/mL) |
|---|---|---|
| Dispersion 22 | 250 | 14,600 |
| Dispersion 23 | 207 | 10,200 |
| Control C2 | 101 | 4200 |

As can be seen from the data, Dispersions 22 and 23 provided concentration enhancement of Drug 2 relative to Control C2. The $MDC_{90}$ provided by Dispersion 22 was 2.5-fold that of Control C2, while the $AUC_{90}$ was 3.5-fold that of Control C2. The $MDC_{90}$ provided by Dispersion 23 was 2.0-fold that of the Control C2, while the $AUC_{90}$ was 2.4-fold that of Control C2.

Dispersion 27 (25:75 Drug 1:Polymer 28) was evaluated in vitro using the microcentrifuge dissolution test described above. The concentrations of Drug 1 obtained were used to determine the $MDC_{90}$ and $AUC_{90}$ values. The results are shown in Table 20. The results for Control C1 (from Table 18) are shown again in Table 20 for comparison.

TABLE 20

| Sample | $MDC_{90}$ (μgA/mL) | $AUC_{90}$ (min · μgA/mL) |
|---|---|---|
| Dispersion 27 | 430 | 35,400 |
| Control C1 | <1 | <100 |

As can be seen from the data, Dispersion 27 provided concentration enhancement of Drug 1 relative to Control C1. The $MDC_{90}$ provided by Dispersion 27 was greater than 430-fold that of Control C1, while the $AUC_{90}$ was greater than 354-fold that of Control C1.

Examples 30-31

Drug 4 (HCl salt form) and $CA_{rk}S$ polymers were weighed into scintillation vials and mixed in a Turbula mixer to form Physical Mixtures 3 and 4, each containing 36 wt % of active Drug 4 (wt % "active" drug means weight of drug excluding weight of salt species). The Physical Mixtures were evaluated in vitro using the membrane permeation test described above, except that the permeate solutions consisted of 60 wt % decanol in n-decane, and the feed solutions consisted of the MFD solution described above. For these tests, had all of the drug dissolved, the concentration of Drug 4 in the feed solutions would have been 100 μgA/mL. Control C4 consisted of crystalline Drug 4 alone; had all of the drug dissolved, the concentration of Drug 4 added would have been 100 μgA/mL Drug 4.

The maximum flux of drug across the membrane (in units of $ggA/cm^2$-min) was determined by estimating the tangent to the concentration versus time curve at time 0. The results are summarized in Table 21, and show that Physical Mixtures 3 and 4 of Drug 4 and the $CA_{rk}S$ polymers of the present invention provided concentration enhancement relative to the crystalline drug Control C4, providing a maximum flux of drug that was 1.32- and 1.85-fold, respectively, that of the control.

TABLE 21

| Physical Mixture | Formulation | Feed Solution | Maximum Drug Flux (μgA/cm²-min) |
|---|---|---|---|
| 3 | 36% A Drug 4 + Polymer 27 | 0.5% NaTC/POPC | 0.21 |
| 4 | 36% A Drug 4 + Polymer 21 | 0.5% NaTC/POPC | 0.30 |
| C4 | Crystalline Drug 4 | 0.5% NaTC/POPC | 0.16 |

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

The invention claimed is:

1. A composition comprising
   (a) a low-solubility drug, said drug having a minimum aqueous solubility of 0.5 mg/mL or less, and
   (b) a cellulose alkanyl succinate polymer having a degree of substitution of alkanyl groups of at least 1.0 and a degree of substitution of succinyl groups of at least 0.2;
   wherein said polymer and said drug are in the form of a solid amorphous dispersion.

2. The composition of claim 1 wherein the degree of substitution of alkanyl groups is at least 1.25 and the degree of substitution of succinyl groups is at least 0.25.

3. The composition of claim 1 wherein the ratio of the degree of substitution of alkanyl groups to the degree of substitution of succinyl groups is less than 7.

4. A composition comprising
   (a) a low-solubility drug, said drug having a minimum aqueous solubility of 0.5 mg/mL or less, and
   (b) a methyl cellulose alkanyl succinate polymer having a combined degree of substitution of methoxy groups and alkanyl groups of at least 1.0 and a degree of substitution of succinyl groups of at least 0.2;
   wherein said polymer and said drug are in the form of a solid amorphous dispersion.

5. The composition of claim 4 wherein said combined degree of substitution is at least 1.25 and said degree of substitution of alkanyl groups is at least 0.25.

6. The composition of claim 4 wherein the ratio of (i) the combined degree of substitution of methoxy groups and alkanyl groups to (ii) the degree of substitution of succinyl groups is less than 7.

7. The composition of claim 1 or 4 wherein said alkanyl groups are selected from the group consisting of acetyl, propionyl and butyryl.

8. The composition of claim 1 or 4 wherein at least a major portion of said drug is amorphous.

* * * * *

UNITED STATES PATENT AND TRADEMARK OFFICE
Certificate

Patent No. 8,617,604 B2                                                                            Patented: December 31, 2013

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Walter Christian Babcock, Bend, OR (US); Dwayne Thomas Friesen, Bend, OR (US); David Keith Lyon, Bend, OR (US); Warren Kenyon Miller, Bend, OR (US); and Daniel Tod Smithey, Bend, OR (US).

Signed and Sealed this Twenty-fifth Day of November 2014.

<div style="text-align:right">

ROBERT A. WAX
*Supervisory Patent Examiner*
Art Unit 1615
Technology Center 1600

</div>